(12) United States Patent
Lim

(10) Patent No.: US 8,391,983 B2
(45) Date of Patent: Mar. 5, 2013

(54) IMPLANTABLE PULSE GENERATOR EMI FILTERED FEEDTHRU

(75) Inventor: Wist Lim, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 990 days.

(21) Appl. No.: 12/425,675

(22) Filed: Apr. 17, 2009

(65) Prior Publication Data
US 2009/0281603 A1 Nov. 12, 2009

Related U.S. Application Data

(63) Continuation-in-part of application No. 12/117,090, filed on May 8, 2008.

(51) Int. Cl.
*A61N 1/08* (2006.01)

(52) U.S. Cl. ............ 607/37; 607/5; 607/9; 607/72

(58) Field of Classification Search .......... 607/37
See application file for complete search history.

(56) References Cited

U.S. PATENT DOCUMENTS

| | | | | |
|---|---|---|---|---|
| 5,032,692 A | * | 7/1991 | DeVolder | 174/50.56 |
| 5,333,095 A | * | 7/1994 | Stevenson et al. | 361/302 |
| 6,026,325 A | * | 2/2000 | Weinberg et al. | 607/36 |
| 6,424,234 B1 | | 7/2002 | Stevenson | |
| 6,999,818 B2 | * | 2/2006 | Stevenson et al. | 607/37 |
| 7,187,974 B2 | * | 3/2007 | Haeg et al. | 607/36 |

* cited by examiner

*Primary Examiner* — Christopher D Koharski
*Assistant Examiner* — Michael Carey

(57) ABSTRACT

Disclosed herein is an implantable pulse generator. The implantable pulse generator may include a header, a can and a feedthru. The header may include a lead connector block electrically coupled to a first conductor. The can may be coupled to the header and include a wall and an electronic component electrically coupled to a second conductor and housed within the wall. The feedthru may be mounted in the wall and include a header side with a first electrically conductive tab and a can side with a second electrically conductive tab electrically coupled to the first tab. The first tab is electrically coupled to the first conductor and the second tab is electrically coupled to the second conductor.

24 Claims, 22 Drawing Sheets

IMPLANTABLE PULSE GENERATOR EMI FILTERED FEEDTHRU

CROSS-REFERENCE TO RELATED APPLICATIONS

This application is a continuation-in-part ("CIP") of copending U.S. patent application Ser. No. 12/117,090, filed May 8, 2008, and is hereby incorporated by reference in its entirety.

FIELD OF THE INVENTION

The present invention relates to medical apparatus and methods. More specifically, the present invention relates to feedthrus for implantable pulse generators and methods of manufacturing such feedthrus.

BACKGROUND OF THE INVENTION

Implantable pulse generators, such as pacemakers, defibrillators or implantable cardioverter defibrillators ("ICD"), are used to provide electrotherapy to cardiac tissue via implantable medical leads. An implantable pulse generator feedthru is used for an electrical pathway extending between the electrically conductive lead securing components of a header of the pulse generator and the electrical components, such as an output flex, hybrid, etc., hermetically sealed in the housing or can of the pulse generator.

Feedthrus are mounted in the wall of the housing or can and include feedthru wires extending through the feedthrus. Feedthrus provide insulated passageways for feedthru wires, such as platinum iridium (Pt/Ir) wires, through the wall of the can. The header ends of the feedthru wires are electrically connected to connector blocks that mechanically and electrically couple with connector ends of implantable medical leads, and the can ends of the feedthru wires are electrically connected to the electrical components housed in the can of the pulse generator.

There are a number of disadvantages associated with current feedthru designs. First, current feedthrus have feedthru wires that extend through the feedthru, which is an expensive configuration due to the labor involved with manufacturing and the substantial lengths of Pt/Ir wire needed for such feedthru wires. Second, current feedthrus employ discoidal filter assemblies for filtering out unwanted signals, such as those associated with electromagnetic interference ("EMI"). Discoidal filter assemblies have high associated material and manufacturing costs.

There is a need in the art for a feedthru that has reduced material and manufacturing costs. Also, there is a need in the art for a method of manufacturing such a feedthru.

BRIEF SUMMARY OF THE INVENTION

Disclosed herein is an implantable pulse generator. In one embodiment, the implantable pulse generator includes a header, a can and a feedthru. The header may include a lead connector block electrically coupled to a first conductor. The can may be coupled to the header and include a wall and an electronic component electrically coupled to a second conductor and housed within the wall. The feedthru may be mounted in the wall and include a header side with a first electrically conductive tab and a can side with a second electrically conductive tab electrically coupled to the first tab. The first tab is electrically coupled to the first conductor and the second tab is electrically coupled to the second conductor. In one embodiment, a chip capacitor may be located on a can side of the feedthru.

Disclosed herein is an implantable pulse generator feedthru. In one embodiment, the feedthru includes: an electrically insulating body including a header side and a can side; a ground circuit at least a portion of which is on the body; and a power circuit including a first tab on one of the sides. In one embodiment, the feedthru may further include a chip capacitor coupled to the body and including a power side electrically coupled to the power circuit and a ground side electrically coupled to the ground circuit.

Disclosed herein is an implantable pulse generator feedthru. In one embodiment, the feedthru includes: an electrically insulating body including a header side and a can side; a ground side conductive path operably coupled to the body; and a power side conductive path extending through the body, wherein the conductive path is not a feedthru wire. In one embodiment, the feedthru further includes a chip capacitor coupled to the body and including a power side electrically coupled to the power side conductive path and a ground side electrically coupled to the ground side conductive path.

Disclosed herein is an implantable pulse generator. In one embodiment, the pulse generator includes a header, a can, a feedthru, and a chip capacitor. The header may include a lead connector block electrically coupled to a first conductor. The can may be coupled to the header and include a wall and an electronic component electrically connected to a second conductor and housed within the wall. The feedthru may be mounted in the wall and comprises an electrically insulating core and a power circuit. The chip capacitor may be mounted on the feedthru. The core may include a first side, a second side generally opposite the first side, and a third side generally lateral the second side. The power circuit may extend between the three sides. The first conductor may be electrically connected to the power circuit at the first side. The second conductor may be electrically connected to the power circuit at the third side. The power side of the chip capacitor may be electrically connected to the power circuit at the second side.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1:
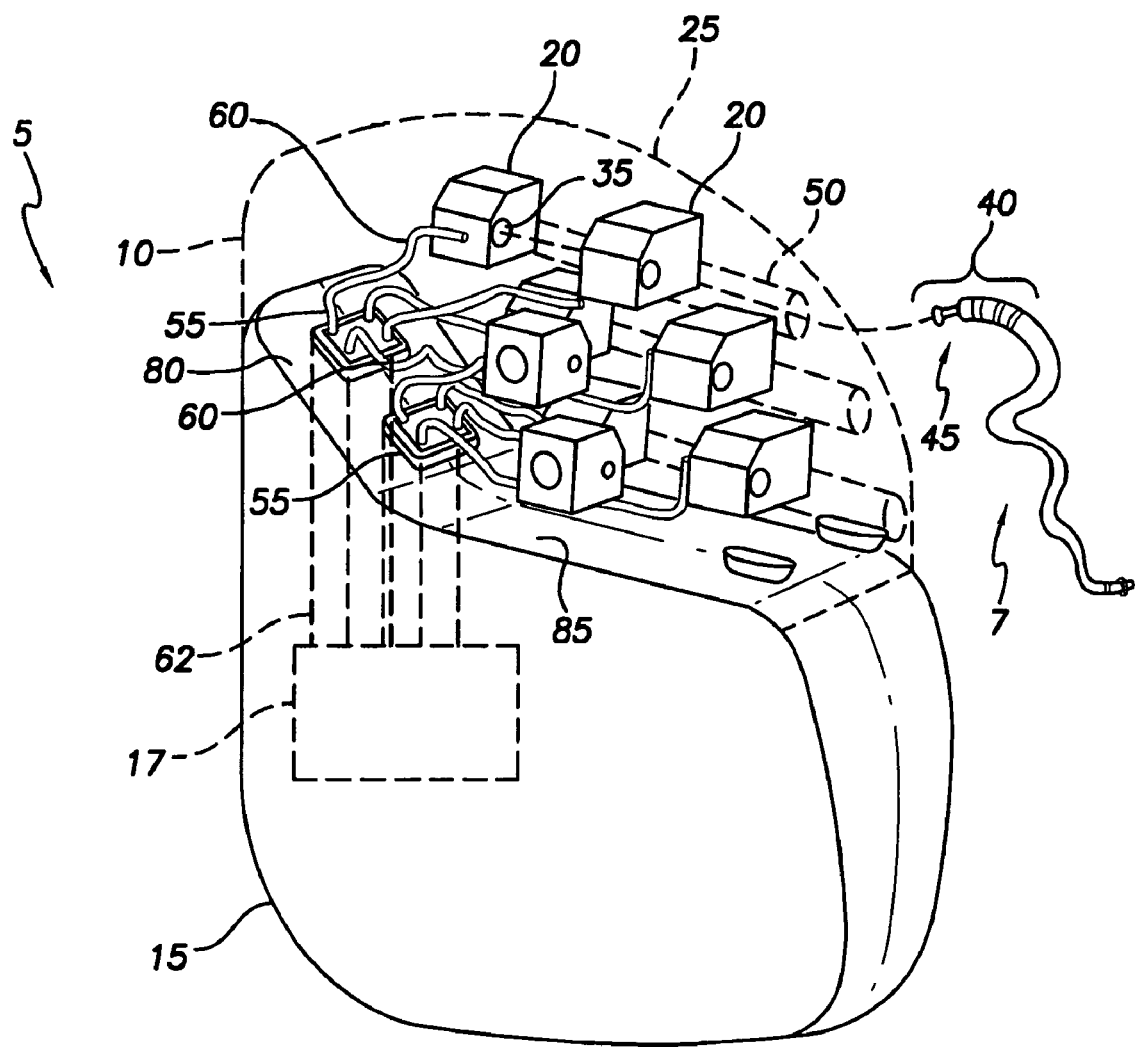
FIG. 1 is an isometric view of an implantable pulse generator employing a feedthru according to the present disclosure.

The present disclosure describes a feedthru 55 of an implantable pulse generator 5 such as a defibrillator, a pacemaker or an ICD. The feedthru 55 disclosed herein includes tabs 70 for electrical communication between the components of the header 10 (e.g., the connector blocks 20) and the electrical components 17 (e.g., output flex, hybrid, etc.) housed within the can 15. The feedthru 55 provides an electrically insulated passageway for electrical communication via the tabs 70 through the can wall 65.

Generally, the tabs 70 and the components 20, 17 of the header 10 and the can 15 are in electrical communication via conductors 60, 62 such as round wire, flat ribbon wire, flex cable, etc. The feedthru 55 reduces manufacturing and material costs because it does not employ feedthru wires, which are typically made of expensive Pt/Ir. The feedthru 55 further reduces material and design costs by utilizing an off-the-shelf chip capacitor 90 as an EMI filter element, the chip capacitor 90 being less expensive than a discoidal capacitor with respect to material and manufacturing costs. Due in part to its lack of feedthru wires, the feedthru 55 is generally compact and low profile and can therefore be installed in the inclined portion 80 and/or the flat portion 85 of the can 15 or any other part of the can 15 including the vertical side walls.

For a general discussion of an implantable pulse generator 5 that utilizes the feedthru 55 disclosed herein, reference is first made to FIG. 1, which is an isometric view of such an implantable pulse generator 5. As indicated in FIG. 1, the pulse generator 5 includes a header 10 and a can or housing 15. The header 10 includes connector blocks 20 and a molded portion 25 (shown in phantom) that encloses the blocks 20. Each block 20 includes an opening 35 configured to receive therein and mate with a connector end 40 of a lead proximal end 45, thereby forming an electrical connection between the connector block 20 and the lead connector end 40 and mechanically securing the proximal end 45 of the lead 7 to the header 10 of the pulse generator 5.

The header molded portion 25 (shown in phantom) may be formed of a polymer material. Passages 50 (shown in phantom) extend from the exterior of the molded portion 25 to the openings 35 in the blocks 20, providing a pathway for the lead distal ends 40 to pass through the molded portion 25 and enter the openings 35.

The can 15 includes feedthrus 55 mounted in the wall of the can 15. Conductors 60 (e.g., round wires, flat ribbon wires, flex cables or etc.) extend from the header sides of the feedthrus 55 to respective connector blocks 20. The can 15 provides a hermetically sealed enclosure for the pulse generator's electronic components 17 (e.g., output flex, hybrid, or various other electronic components) housed within the can 15. Conductors 62 (e.g., round wires, flat ribbon wires, flex cables or etc.) extend from the can sides of the feedthrus 55 to the electronic components 17. Typically, the wall of the can 15 is made of titanium or another biocompatible metal.

As shown in FIG. 1, in one embodiment, the feedthrus 55 are mounted in an inclined portion 80 of the can 15. In other embodiments, the feedthrus 55 may be mounted in a flat portion 85 of the pulse generator 5, or the feedthrus 55 may be mounted in both the inclined and flat portions 80, 85 of the can 15. In yet other embodiments, the feedthrus 55 may be mounted on the vertical side walls of the can 15.

Figure 2A:
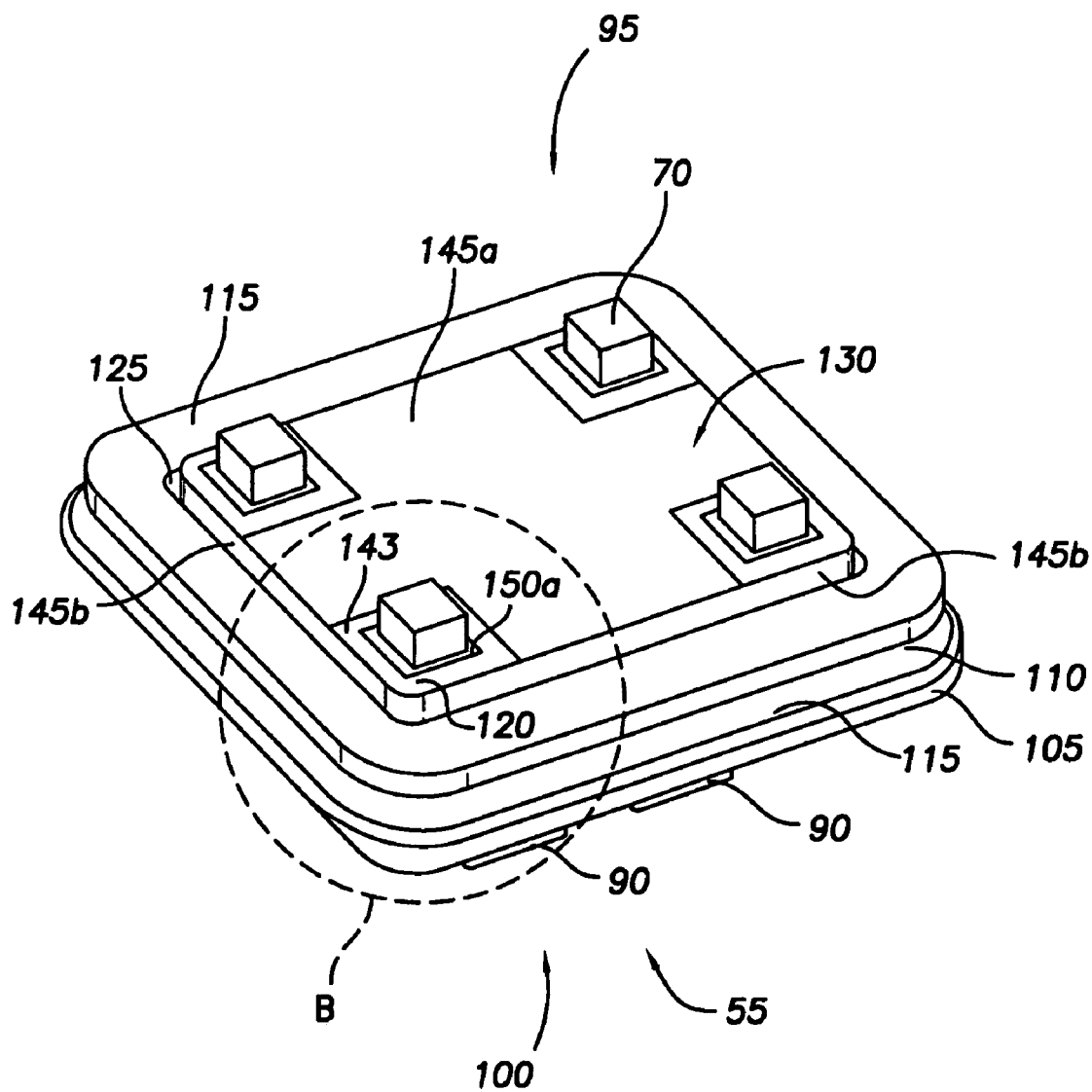
FIG. 2A is a top isometric view of the feedthru of FIG. 1.
Figure 2B:
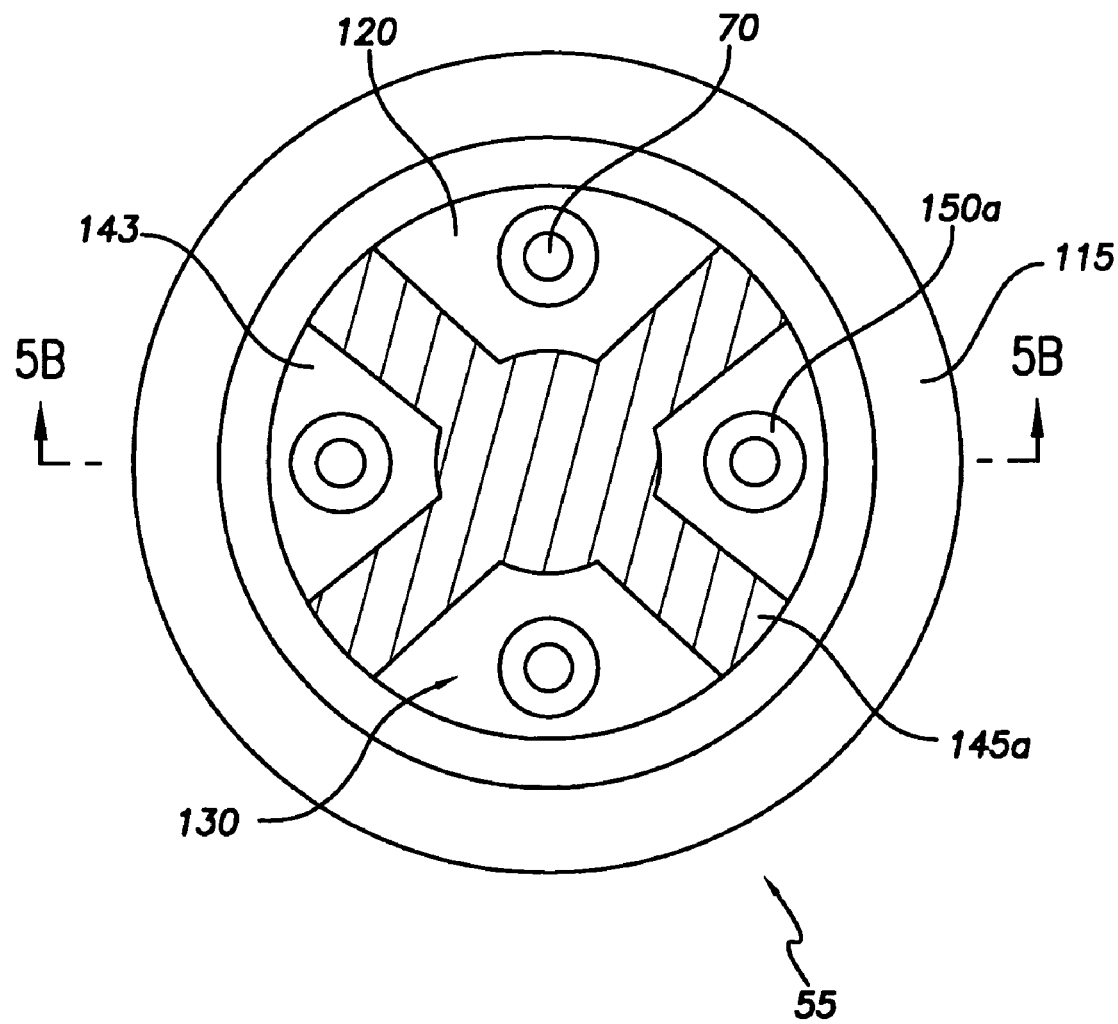
FIG. 2B is a top plan view of an alternative embodiment of the feedthru of FIG. 1.
Figure 3A:
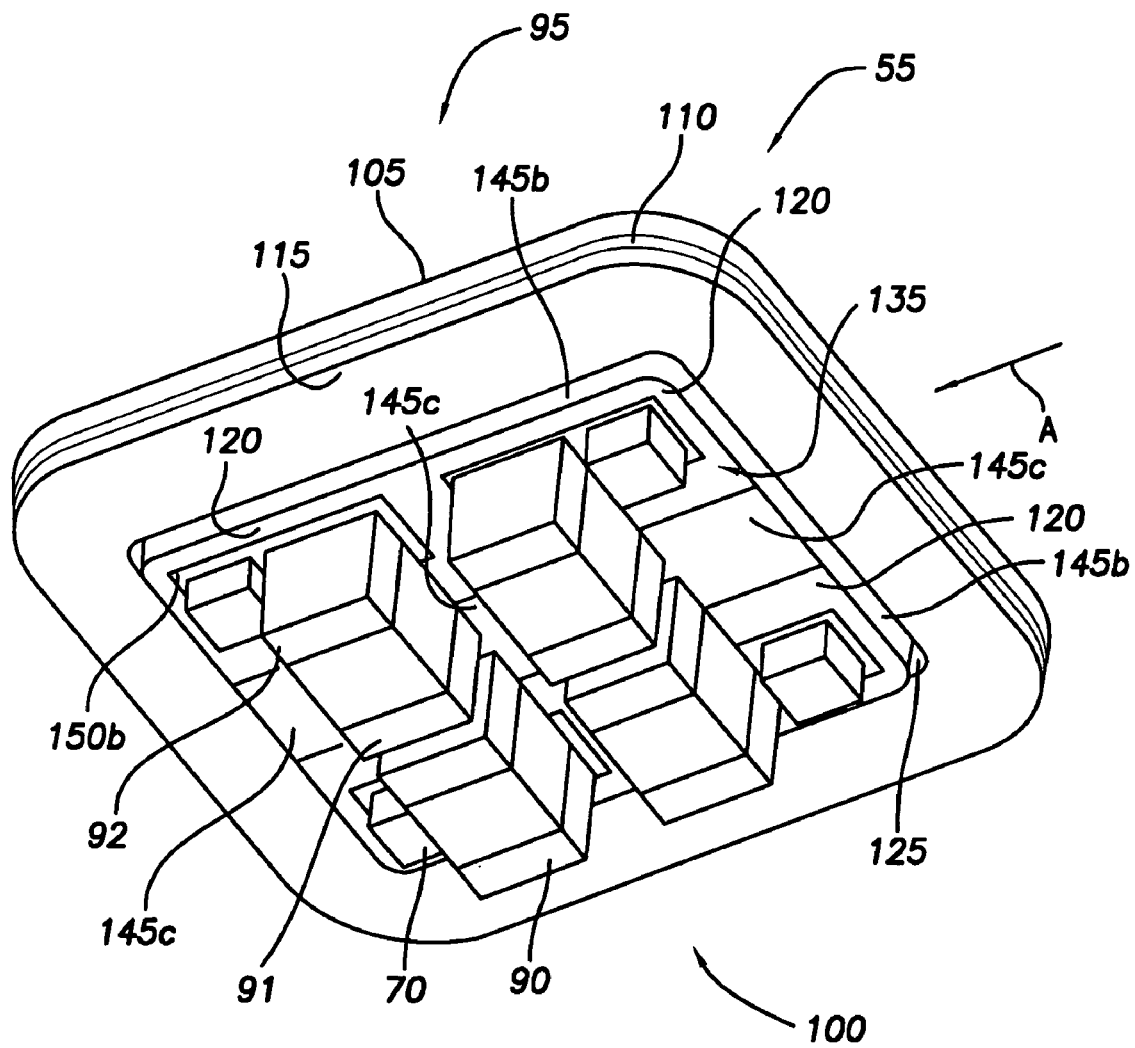
FIG. 3A is a bottom isometric view of the feedthru of FIG. 1.
Figure 3B:
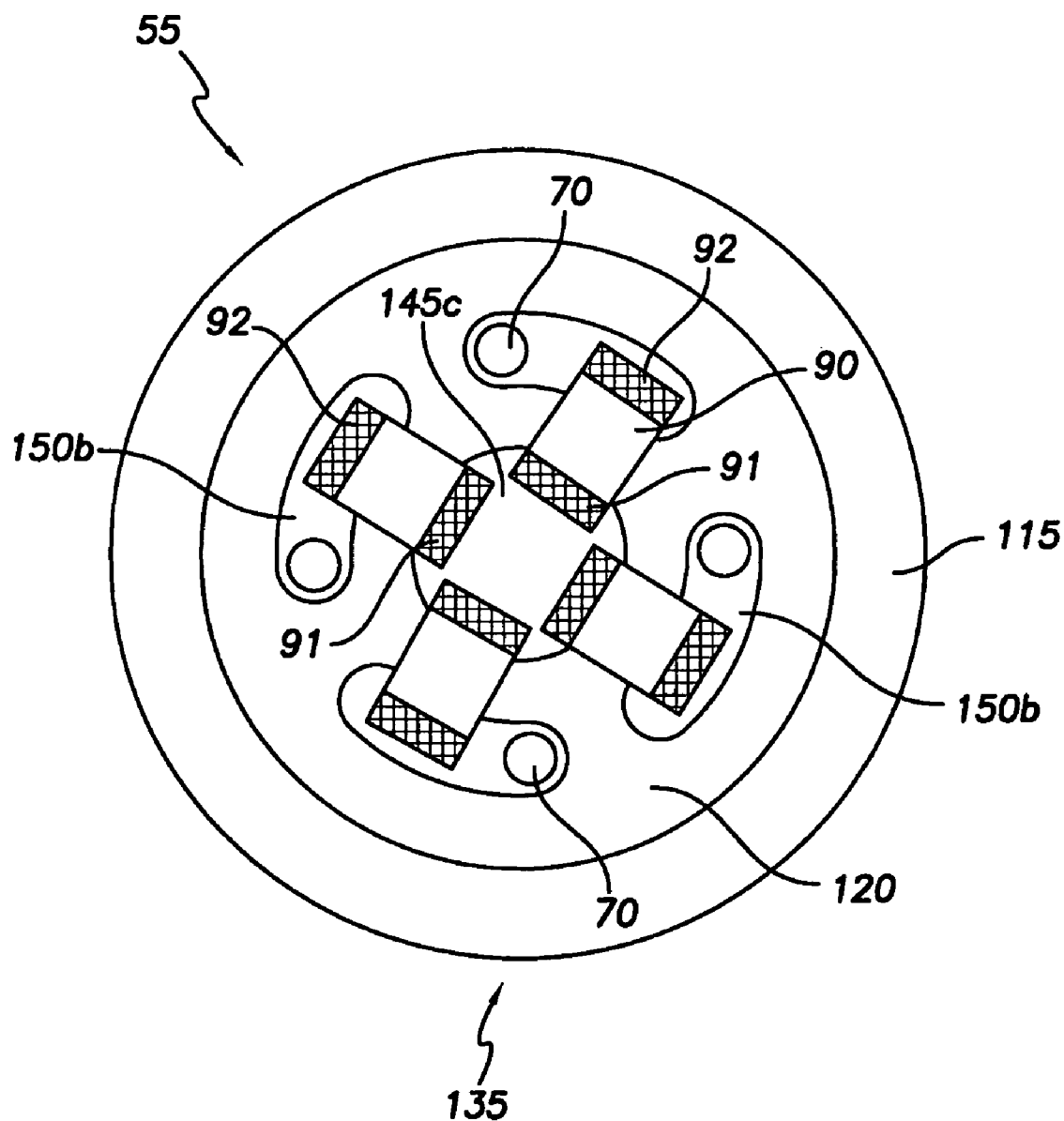
FIG. 3B is a bottom plan view of an alternative embodiment of the feedthru of FIG. 1.
Figure 4:
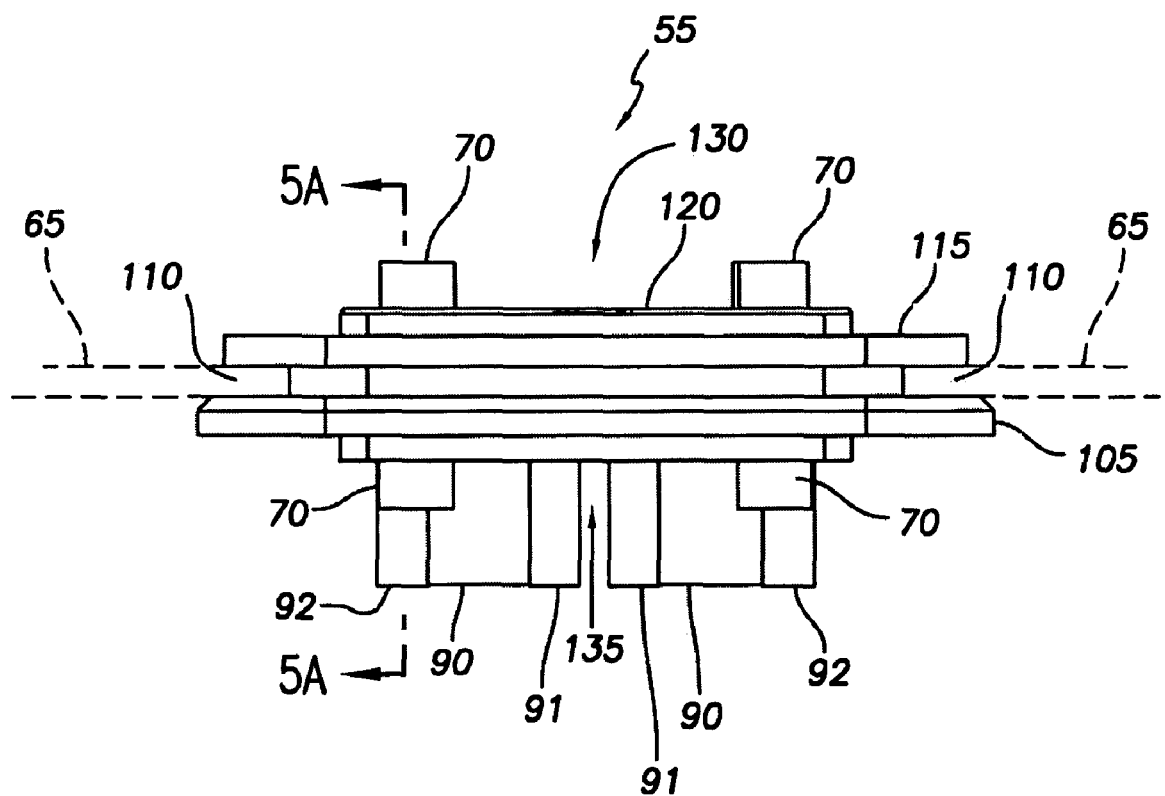
FIG. 4 is a side view of the feedthru taken from the direction of arrow "A" of FIG. 3A.
Figure 5A:
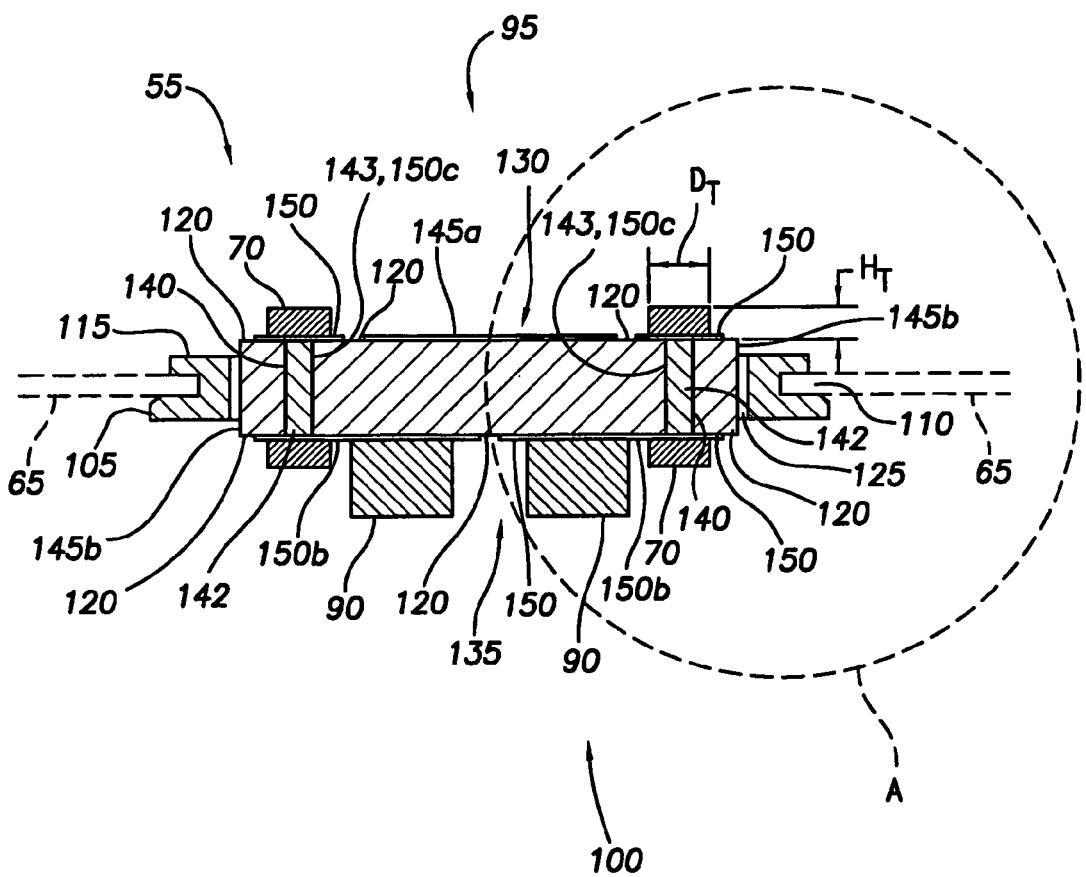
FIG. 5A is a longitudinal cross-sectional elevation of the feedthru as taken along section line 5A-5A of FIG. 4.
Figure 5B:
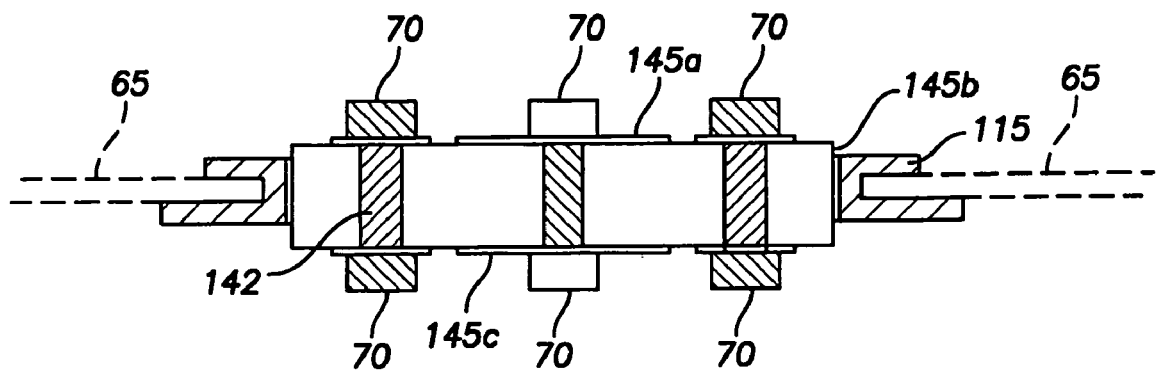
FIG. 5B is a longitudinal cross-sectional elevation of an alternative embodiment of the feedthru as taken along section line 5B-5B of FIG. 2B, wherein the chip capacitors are not shown for clarity purposes.

For a detailed discussion of the components of the feedthru 55, reference is now made to FIGS. 2A-5B. FIG. 2A and FIG. 3A are, respectively, top and bottom isometric views of the feedthru 55 of FIG. 1. FIG. 2B and FIG. 3B are, respectively, top and bottom plan views of an alternative embodiment of the feedthru 55 of FIG. 1. FIG. 4 is a side view of the feedthru 55 taken from the direction of arrow "A" of FIG. 3A. FIG. 5A is a cross-sectional elevation of the feedthru 55 as taken along section line 5A-5A of FIG. 4. FIG. 5B is a longitudinal cross-sectional elevation of an alternative embodiment of the feedthru 55 as taken along section line 5B-5B of FIG. 2B, wherein the chip capacitors 90 are not shown for clarity purposes.

In one embodiment, as shown in FIGS. 2A, 3A and 4, the feedthru 55 includes a header side 95, a can side 100 and a lateral or edge side 105 that forms a rectangular or square edge or boarder of the feedthru 55. As can be understood from FIGS. 2B, 3B and 5B, in an alternative embodiment, the edge side 105 may form a circular or rounded edge or boarder of the feedthru 55. As indicated in FIGS. 4 and 5A, the edge side 105 may vary in diameter to define a slot or groove 110 that receives the wall 65 of the can 15 when the feedthru 55 is assembled into the can 15 of the pulse generator 5.

As can be understood from FIGS. 2A-5B, the feedthru 55 includes a feedthru housing 115, a core 120, chip capacitors 90, tabs 70 and ground and power circuits. The housing 115 forms the edge side 105 of the feedthru 55 and includes a central or core-receiving opening 125. The housing 115 may be machined, molded or otherwise formed to fit the space and design constraints of an implantable pulse generator 5. The housing 115 may be titanium, a titanium alloy, MP35N, or stainless steel.

The outer edge or boundary of the housing 115 is defined by the edge side 105 and includes the groove or slot 110 that receives the can wall 65 when the feedthru is mounted in the can wall. The central opening 125 of the housing 115 extends axially through the housing and defines a void that is occupied by the core 120.

As shown in FIGS. 2A-5B, the core 120 includes a header face 130, a can face 135, and through-holes 140 extending axially therethrough. The core 120 may be formed of an electrically insulating material, such as ceramic, glass, or sapphire.

As can be understood from FIGS. 1-5B, the feedthru 55 includes a power circuit and a ground circuit. The power circuit includes the tabs 70, their respective vias 142 and power traces 150. The tabs 70 are electrically coupled to each other by their respective vias 142, and the power traces 150 electrically couple the tabs 70 to the power sides 92 of the chip capacitors 90 located on the feedthru 55. The power circuit, via the tabs 70, electrically couples the power sides of the electrical components 17 housed in the can wall 65 to the lead connector blocks 20 of the header 10.

The ground circuit includes the feedthru housing 115 and ground traces 145 electrically coupled to the feedthru housing 115. The ground traces 145 electrically couple the ground sides 91 of the chip capacitors 90 to the feedthru housing 115, which is electrically coupled to the can wall 65. A detailed discussion regarding each of the components of the power and ground circuits is given below.

As indicated in FIGS. 2A-5B, the electrically conductive tabs 70 may be located on one or both of the faces 130, 135 of the core 120. For example, tabs 70 may be located near each of the four corners of each face 130, 135. The tabs 70 may be arranged such that a tab 70 on the header face 130 near a first corner of the feedthru 55 is located directly across the core from a tab 70 mounted on the can face 135 near the same first corner, thereby forming a pair of tabs 70. Such a paired arrangement may be provided at each of the four corners of the feedthru 55.

While in some embodiments, as illustrated in FIGS. 2A-3B, the tabs 70 are located near outside edges of the core header face 130 and core can face 135, in alternative embodiments, the tabs 70 may be located closer to the centers of the core header face 130 and core can face 135. In still other embodiments, tabs 70 may be located near both the centers and the outside edges of the core header face 130 and core can face 135. In other embodiments, the tabs 70 may be located in other configurations or locations as long as there is sufficient space for connection of the conductors 60, 62 to the tabs 70.

As can be understood from FIGS. 2A-3B, the number of tabs 70 on the core header face 130 generally corresponds to the number of tabs 70 on the core can face 135. In one embodiment, there are four tabs 70 on the core header face 130 and a corresponding four tabs 70 on the core can face 135. In some embodiments, there are less than four tabs 70 or more than four tabs 70 on each of the core header face 130 and the core can face 135.

Figure 6A:
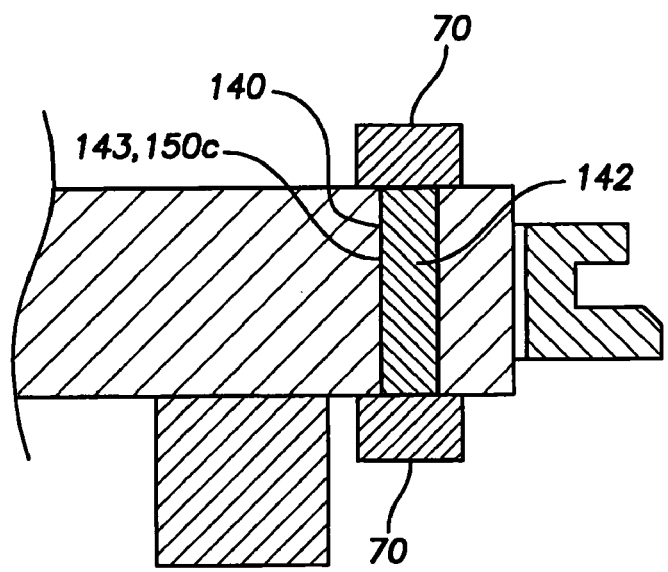
FIGS. 6A-6F are cross-sectional views of alternative tab/via configurations as if viewed in region A of FIG. 5A.

As indicated in FIGS. 5A and 5B, electrically conductive vias 142 extend through the through-holes 140 to electrically couple together the tabs 70 of each pair of tabs 70. The vias 142 and the associated tabs 70 may have a variety of configurations as shown in FIGS. 6A-6F, which are cross-sectional views of alternative tab configurations as if viewed in region A of FIG. 5A. For example, as indicated in FIG. 6A, the vias 142 may be a solid member 142 formed of electrically conductive material such as titanium, stainless steel, MP35N, etc. or a solid member formed of electrically or non-electrically conductive material coated with an electrically conductive material, such as gold, nickel, platinum, etc., where such coating is provided via electroplating, photo deposition, vapor deposition, etc. The surfaces of the through-holes 140 may additionally be coated with an electrically conductive material 143, such as gold, nickel, platinum, etc., where such coating is provided via electroplating, photo deposition, vapor deposition, etc. Such solid member vias 142 may be brazed (including gold brazed), welded or epoxied into the through-holes 140.

Figure 6B:
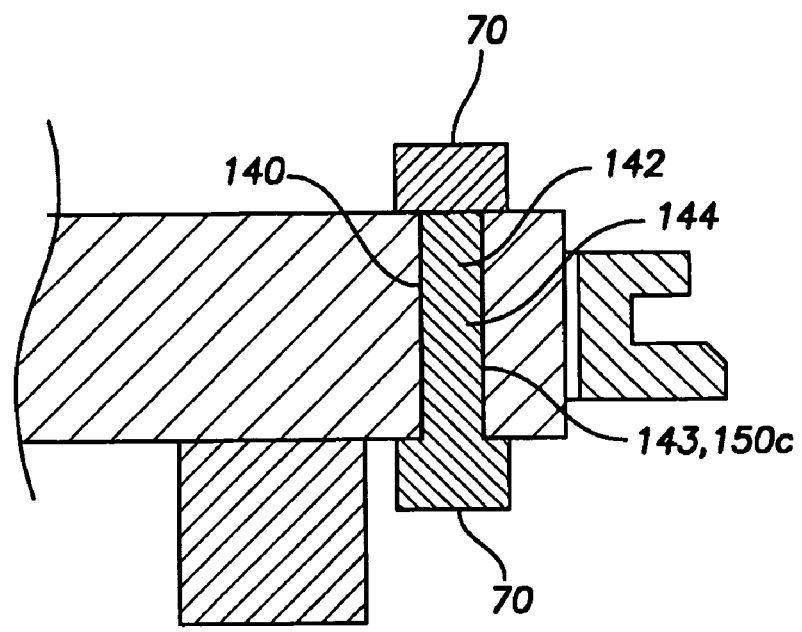
Figure 6C:
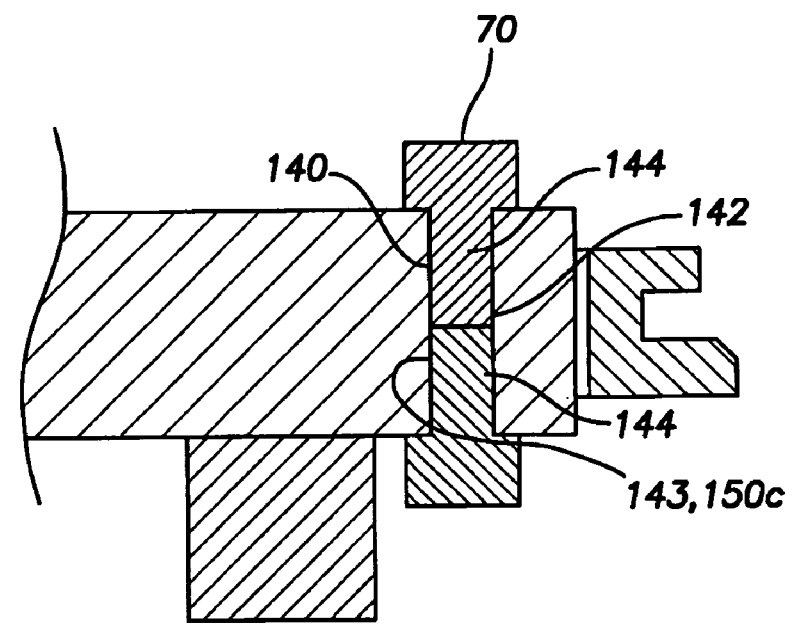

While the solid member vias 142 depicted in FIG. 6A may be a body that is a separate piece from the tabs 70 such that generally no portion of a tab 70 extends into a through-hole 140. As shown in FIGS. 6B and 6C, a portion 144 of a tab 70 may extend into the through-hole 140 to form at least a portion of a solid member via 142. For example, as depicted in FIG. 6B, the entirety of a solid member via 142 may be an extension 144 of a tab 70. Similarly, as illustrated in FIG. 6C, a portion of a solid member via 142 may be an extension 144 of both its respective tabs 70, each tab forming a portion of the solid member via 142. The tab 70 may also be a continuous, solid body extending all the way through the core 120 and also forming the solid member via 142. As shown in FIG. 6F, the diameter of the tab 70 may be the same as the diameter of the via 142. As can be understood from FIG. 6F, such a continuous, solid body tab 70 may be brazed to the through-hole 140 of the core 120. The solid body tab 70 may be made of titanium, MP35N, stainless steel, etc.

Figure 6D:
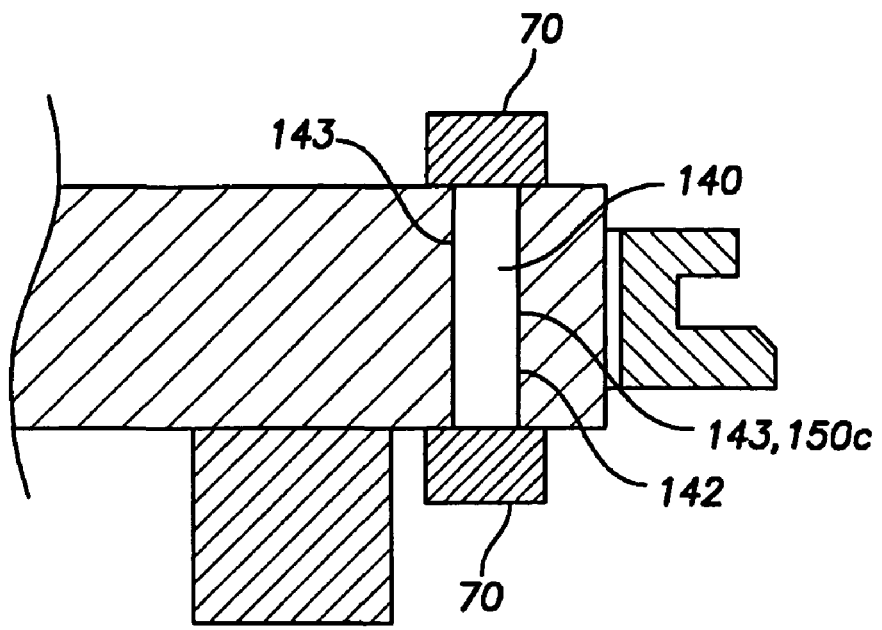

As shown in FIG. 6D, the vias 142 may be a hollow shaft extending axially through the core 120, wherein the surfaces of the hollow shafts are coated with an electrically conductive material 143 to form an electrically conductive trace or coating over on the surfaces of the hollow shafts. The vias 142 may be brazed, welded or secured to the tabs 70 via an electrically conductive epoxy.

Figure 6E:
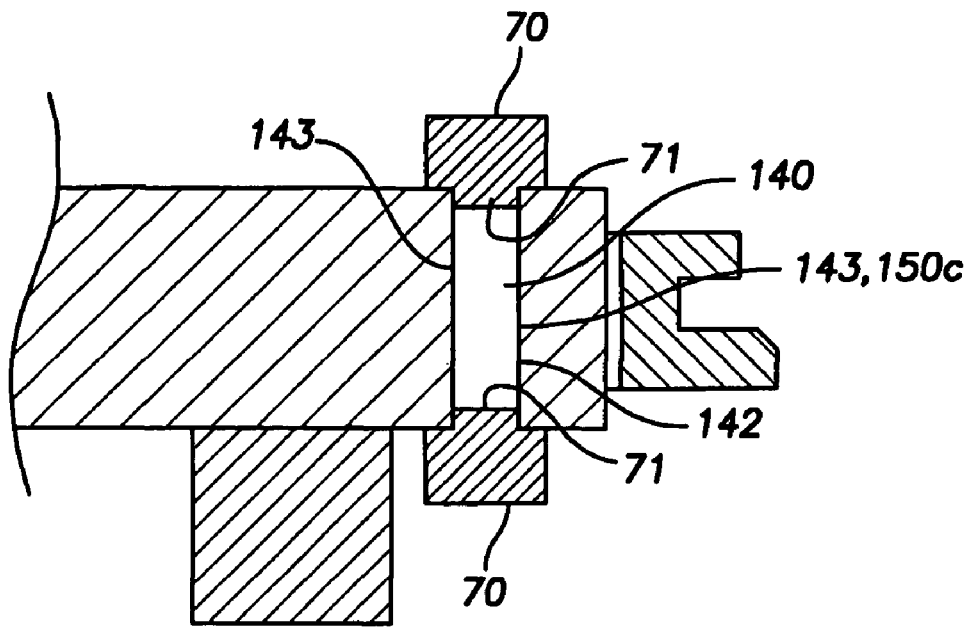
Figure 6F:
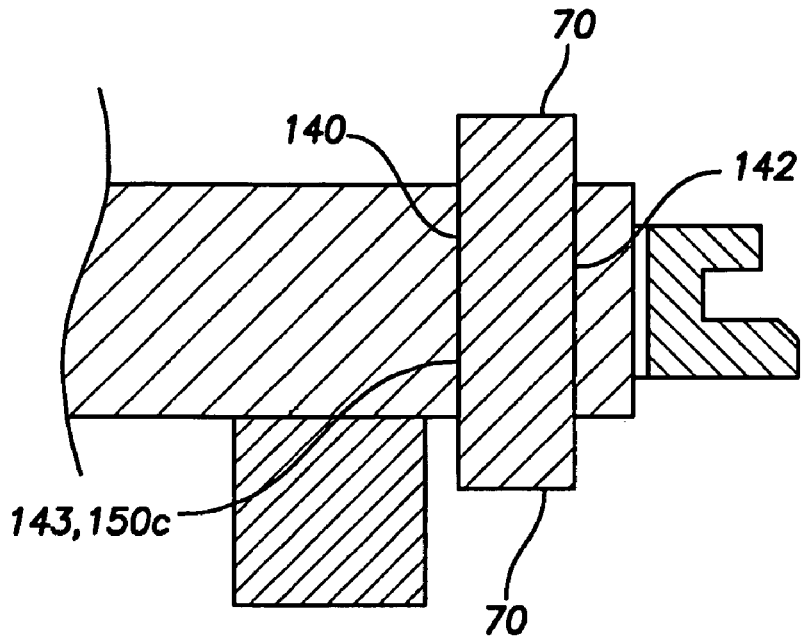

As shown in FIG. 6E, in the vias 142 and tabs 70 may be a combination of the concepts shown in FIGS. 6B-6D, such that the tabs 70 partially extend into the through-holes 140 as nubs 71 and the through holes 140 with their electrically conductive coatings that serve as vias 142 complete the electrical connections between opposed nubs 71. Thus, the vias 142 could be described as a combination of electrically conductive coatings and nubs.

As can be understood from FIGS. 1 and 2A and 2B, conductors 60 leading to the connector blocks 20 are electrically connected via welding, brazing, etc. to the tabs 70 on the header face 130 of the core 120. In a similar fashion and as can be understood from FIGS. 1 and 3A and 3B, conductors 62 leading to the electrical components 17 (e.g. the output flex, hybrid, etc.) housed in the can 15 are electrically connected via welding, brazing, etc. to the tabs 70 on the can face 135 of the core 120. Thus, the tabs 70 and vias 142 provide an electrical pathway through the feedthru 55 to electrically couple the conductors 60, 62 and the connector blocks 20 and components 17 electrically coupled to the conductors 60, 62. As can be understood from FIGS. 1-5B, in at least some of the embodiments of the feedthrus 55 disclosed herein, the feedthrus 55 do not employ feedthru wires.

As can be understood from FIG. 5A, the tabs or posts 70 have a height $H_T$ of between approximately 0.01 in. and approximately 0.05 in. and a diameter $D_T$ of between approximately 0.03 in. and approximately 0.05 in. In one embodiment, the tabs or posts 70 have a height $H_T$ of approximately 0.02 in. and a diameter $D_T$ of approximately 0.03 in. The tabs 70 may be formed of titanium, kovar, stainless steel, MP35N, platinum or gold. The tabs 70 may be brazed, welded or secured to the core faces 130, 135 via an electrically conductive epoxy. In one embodiment, the via 142 may have a length that is generally the same as the thickness of the core 120, e.g., 0.06 in. In one embodiment, the via 142 may have a diameter of 0.015 in.

Figure 7A:
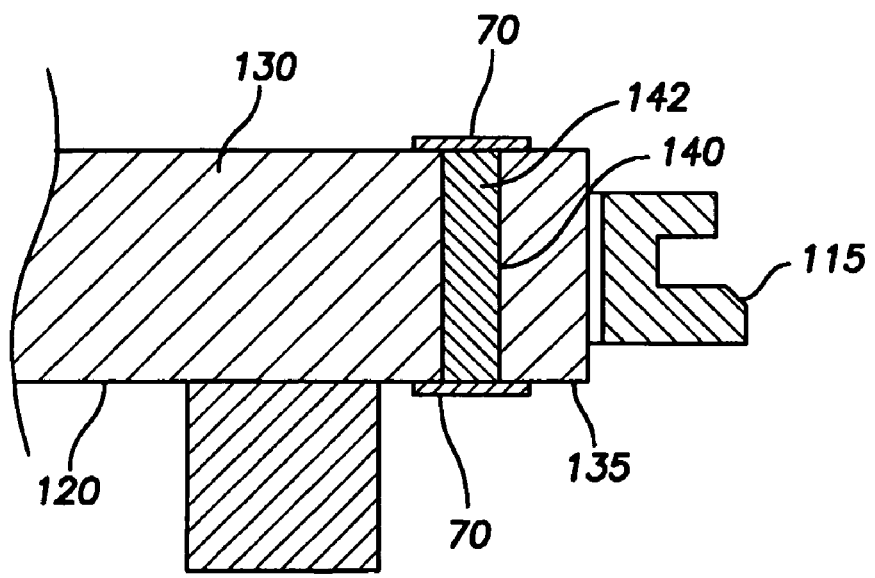
FIG. 7A is a cross-sectional view of a low-relief generally flush tab configuration as if viewed in region A of FIG. 5A.
Figure 7B:
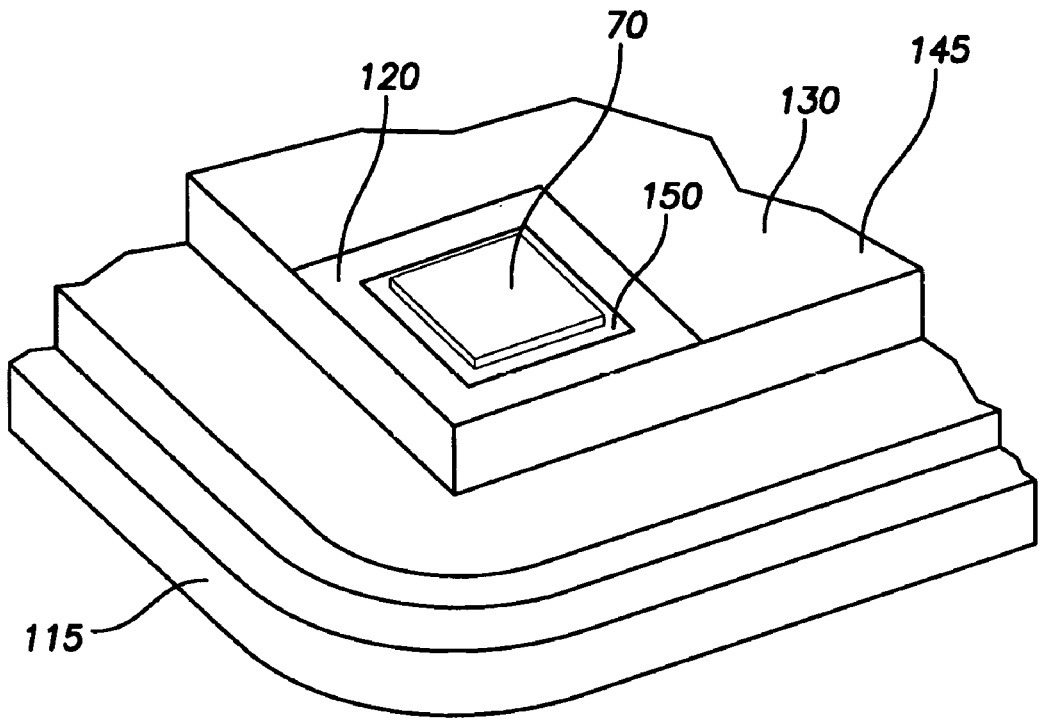
FIG. 7B is an isometric view of the tab configuration of FIG. 7A as if viewed in region B of FIG. 2A.
Figure 7C:
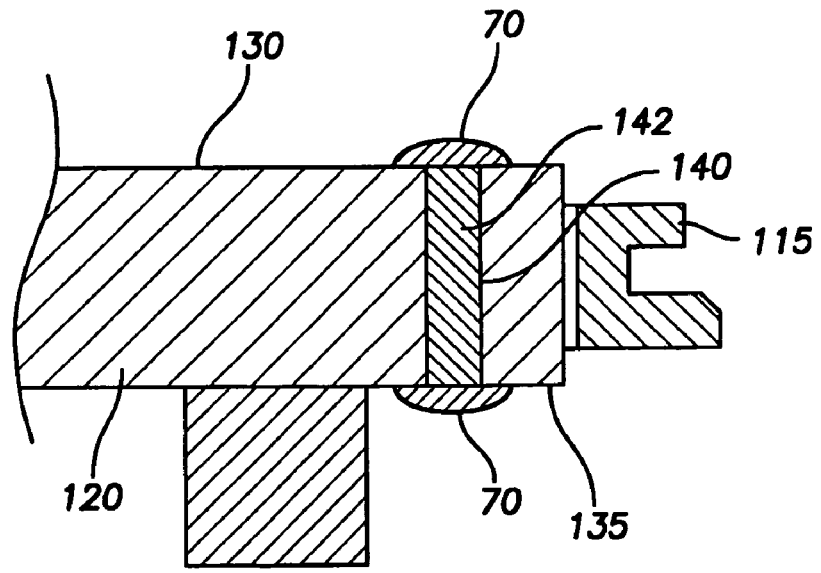
FIG. 7C is a cross-sectional view of a low-relief bump tab configuration as if viewed in region A of FIG. 5A.
Figure 7D:
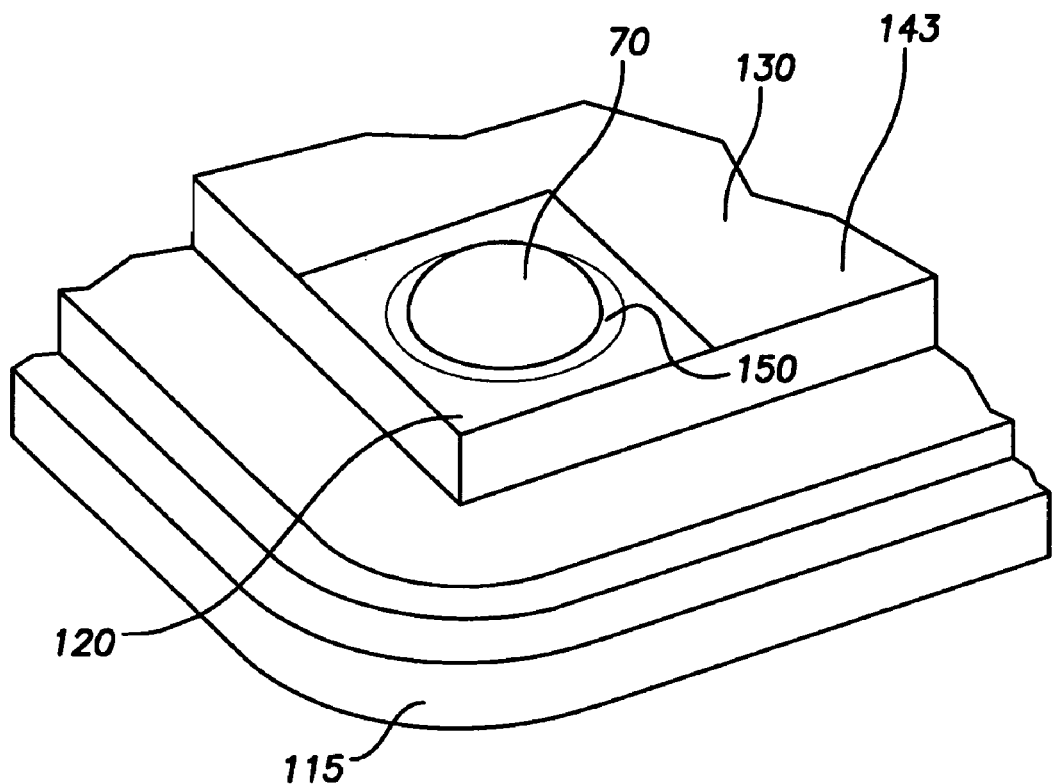
FIG. 7D is an isometric view of the tab configuration of FIG. 7C as if viewed in region B of FIG. 2A.

In some embodiments, as can be understood from FIGS. 7A-7D, which are cross sectional and isometric views, the tabs 70 may have a low surface relief. In some low-relief embodiments, as shown in FIGS. 7A-7B, the tabs 70 may appear flat and perhaps even nearly flush with the core header and can surfaces 130, 135 on which the tabs 70 are mounted. In some other low relief embodiments, as depicted in FIGS. 7A-7B, the tabs 70 may be slightly raised to be bump-like. In any of the embodiments depicted in FIGS. 7A-7D, the low relief tabs 70 may have a circular, rectangular or some other configuration. The low relief tabs 70, whether flush or bump-like, simply serve as locations or features for welding, brazing or other types of attachment to the conductors 60, 62 of the header 10 and can 15.

In some embodiments, as can be understood from FIGS. 2A and 5A and 5B, the tabs 70 may have a post-like configuration that projects a small distance from the core header and can surfaces 130, 135 on which the tabs 70 are mounted and, as a result, are less low-relief than the embodiments discussed with respect to FIGS. 7A-7D. As indicated in FIGS. 2A and 5A, the post-like tabs 70 may be box-like or cubical in shape.

Figure 7E:
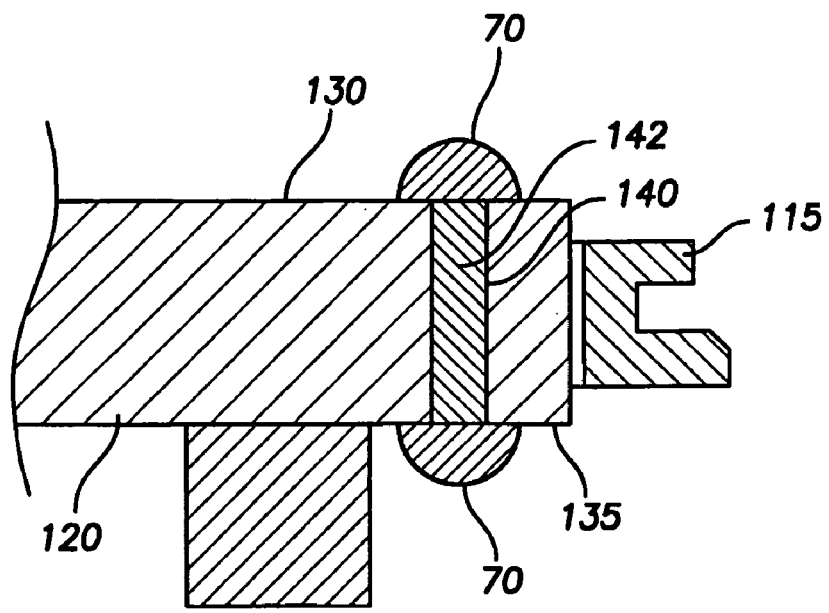
FIG. 7E is a cross-sectional view of post-type tab having a spherical configuration as if viewed in region A of FIG. 5A.
Figure 7F:
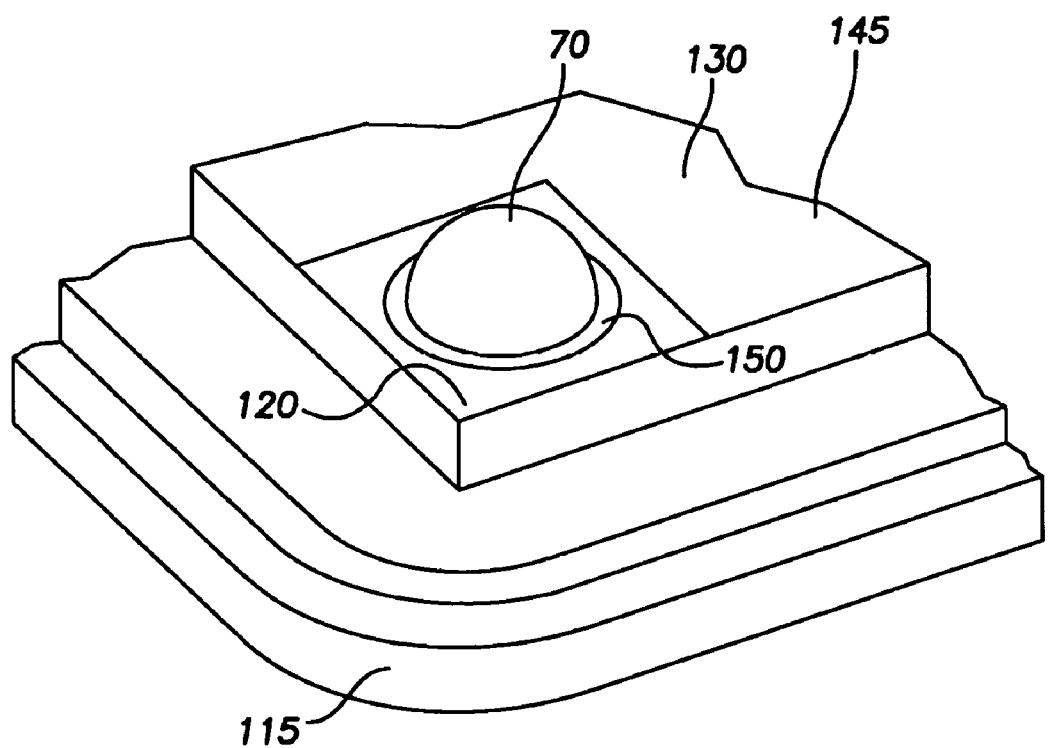
FIG. 7F is an isometric view of the tab configuration of FIG. 7E as if viewed in region B of FIG. 2A.
Figure 7G:
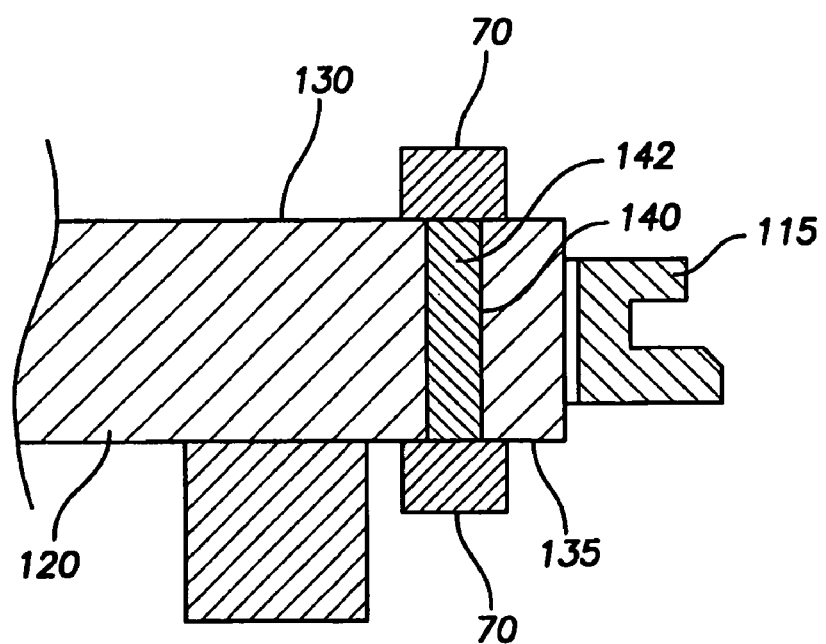
FIG. 7G is a cross-sectional view of a post-type tab having a cylindrical configuration as if viewed in region A of FIG. 5A.
Figure 7H:
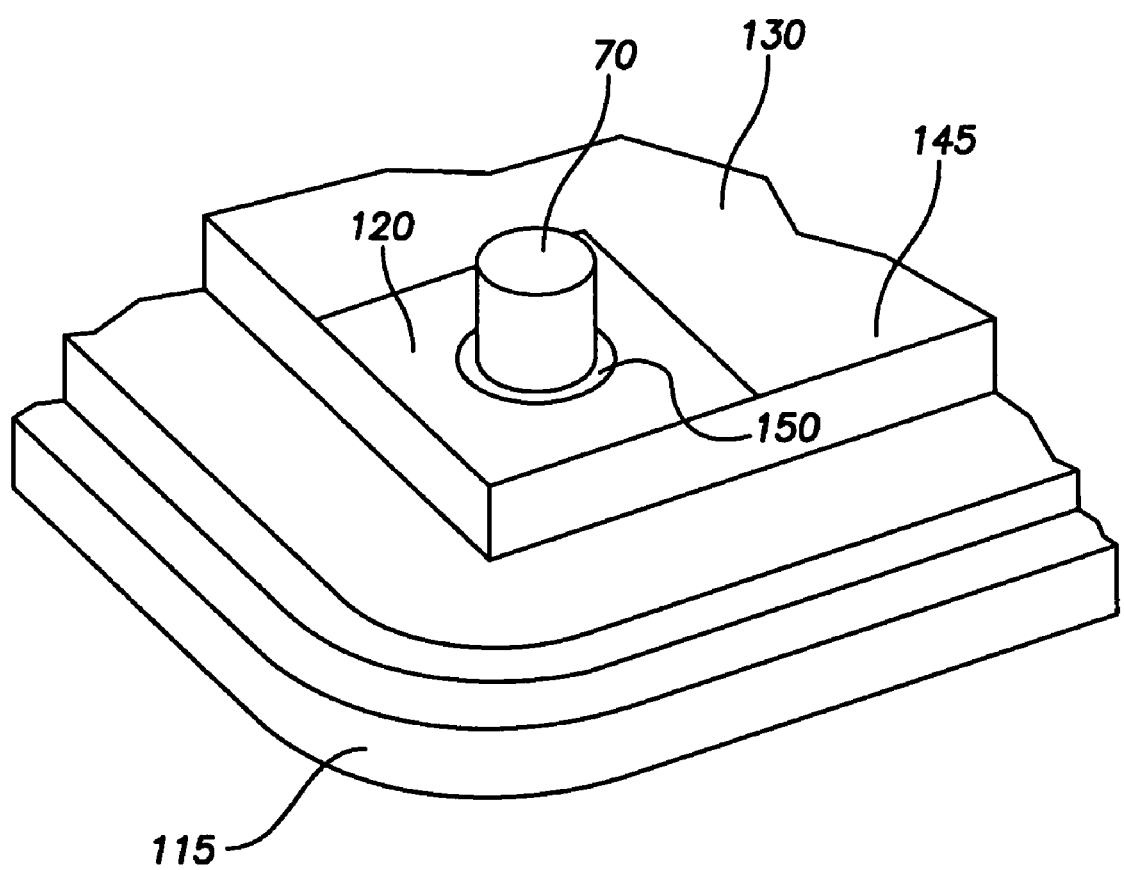
FIG. 7H is an isometric view of the tab configuration of FIG. 7G as if viewed in region B of FIG. 2A.

As can be understood from FIGS. 7E-7H, which are cross sectional and isometric views, the post-like tabs 70 may have other shapes or configurations. For example, as shown in FIGS. 7E-7F, the post-like tabs 70 may be half spherical or another rounded shape. As shown in FIGS. 7G-7H, the post-like tabs 70 may have a cylindrical shape. In other embodiments, the post-like tabs 70 may have other shapes or configurations, such as cubical, half-spherical, cylindrical or some other shape. The post-type tabs 70, whether cubical, half-spherical, cylindrical or some other shape, simply serve as locations or features for welding, brazing or other types of attachment to the conductors 60, 62 of the header 10 and can 15.

While the tab configurations illustrated in FIGS. 2A and 2B, 5A and 5B and 7A-7H show matching tab configurations on each side of the core, in various embodiments, any one, two or more tab configurations depicted in FIGS. 2A and 2B, 5A and 5B and 7A-7H may be combined on a single feedthru 55 or paired with a single via 142. Similarly, while the via configuration depicted in FIGS. 5A and 5B show matching via configurations, any of one, two or more via 142 configurations depicted in FIGS. 6A-6F may be used on a single feedthru 55.

As can be understood from FIGS. 2A and 3A, the outer boarder or edge surface of the core 120 is rectangular and, in one embodiment, square. In an alternative embodiment, as shown in FIGS. 2B and 3B, the outer edge is round or circular. As shown in FIGS. 2A-3B, the outer edge surface of the core 120 projects a small amount past the housing 115 on both the header and can sides 95, 100 of the feedthru such that the outer edge surface of the core 120 is partially exposed and not entirely within housing 115.

As indicated in FIGS. 2A-3B, an electrically conductive ground coating or trace 145 extends over the core outer edge surface, a substantial portion of the core header face 130, and a smaller portion of the core can face 135. In one embodiment, the core header face 130 is generally entirely coated with the ground trace 145a, except in small regions 143 surrounding the tabs 70, wherein the small regions 143 are exposed surfaces of the core 120 electrically isolating the tabs 70 from the ground trace 145.

The ground trace 145b extends along the core outer edge from the core header face 130 to generally cover the entire surface of the core outer edge. The ground trace 145b extending over the core outer edge is in electrical contact with, and brazed or welded to, the housing 115, which is in electrical contact with the can wall 65. The can wall 65 serves as the ground for the pulse generator 5.

The ground trace 145c extends across the center of the core can face 135 from the core outer edge in the form of a rectangular trace 145c, in the context of FIG. 3A, and a round trace 145c, in the context of FIG. 3B. Chip capacitors 90 are located on the core can face 135. The ground trace 145 in all of its locations acts as a portion of the ground circuit, coupling the ground sides 91 of the chip capacitors 90 to the can wall 65 via the feedthru housing 115, which is another portion of the ground circuit. The can wall 65, which is electrically coupled to the feedthru housing 115, serves as the ground for the pulse generator 5. The ground trace 145 in any of its locations may be made of gold, platinum, nickel, titanium, or MP35N. The ground trace 145 in any of its locations may be formed via any method, including photo etching, deposition, electroplating, etc.

As shown in FIGS. 2A and 2B, an electrically conductive power coating or trace 150a boarders each tab 70 and is separated from the adjacent ground trace 145a, 145b by an exposed region 143 of the surface of the electrically insulating core 120. As indicated in FIGS. 3A and 3B, an electrically conductive power trace 150b extends across the core can face 135 from a tab 70 surrounded by the power trace 150b to a power side 92 of a chip capacitor 90. The power trace 150b may extend along the core can face 135 in the form of a rectangle or an oval or other suitable shape.

As indicated in FIGS. 5A-6D, power traces 150c, in the form of electrically conductive coatings 143, may extend along the vias 142 and/or the surfaces of the through-holes 140 to join with the power traces 150a, 150b on the core header and can sides 130, 135. The power traces 150a, 150b, 150c form a power side electrical circuit, along with the tabs 70 and vias 142, that electrically couples the power sides 92 of the chip capacitors 90 with the connector blocks 20 and electrical components 17 via the conductors 60, 62. The power traces 150 may be formed of any electrically conductive material (e.g. gold, platinum, nickel, titanium, MP35N, etc.) capable of being formed into a trace via any method including photo etching, deposition, electroplating, etc.

As can be understood from FIGS. 2A-3B and with reference to FIG. 1, the tabs 70 on the core header face 130 may be electrically connected to the connector blocks 20 by conductors 60, such as round wires, flat ribbon wires or flex cables. At the core can face 135, the tabs 70 may be electrically connected to the electrical components 17 by conductors 62, such as round wires, flat ribbon wires or flex cables or to electrically conductive traces on a printed circuit board. Because the tabs 70 may be electrically connected to each other by vias 142 and electrically connected to the header and can components 20, 17 by less expensive conductors, expensive feedthru wires, such as Pt/Ir wires, are not required in embodiments of the feedthru 55. Therefore, such feedthrus 55 have reduced material and manufacturing costs.

As illustrated in FIG. 3A and 3B, the chip capacitors 90 on the core can face 135 of may include a ground end 91 and a power end 92. The ground end 91 of the chip capacitor 90 is electrically connected to the ground trace 145. The power end 92 of the chip capacitor 90 is electrically connected to the power trace 150. In one embodiment, a first chip capacitor 90 is separated from a second chip capacitor 90 by a minimum of approximately 0.03 in.

The chip capacitors 90 are easy to obtain, that is, they are readily commercially available or "off-the-shelf" chip capacitors. For example, the chip capacitors 90 may be obtained as model 0805 chip capacitor as manufactured by NovaCap of Valencia, Calif. 91355. The chip capacitors 90 are a part of the EMI filter element. EMI is a (usually undesirable) disturbance caused in a radio receiver or other electrical circuit by electromagnetic radiation emitted from an external source. Such a signal may interfere with the electrical components in the can of the implantable pulse generator. Thus, an EMI filter element, such as a chip capacitor, may reduce or eliminate the interference caused by an EMI. Additionally, an "off-the-shelf" chip capacitor may be less expensive and easier to obtain than a discoidal filter assembly, thus reducing the design and manufacturing costs of the feedthru 55.

As can be understood from FIGS. 4 and 5A and 5B, to assemble the feedthru 55, the housing 115 and core 120 may be connected by soldering, brazing, welding or other suitable method to form a housing-core assembly. The coupling of the core 120 to the housing 115 creates a hermetic seal. The tabs 70 may be connected to the core 120 by brazing, soldering, welding or other suitable method. The chip capacitors 90 may be surface mounted or otherwise connected to the can end 135 of the core 120 by soldering, electrically conductive epoxy or other suitable method.

As can be understood from FIGS. 2A-3B, and with reference to FIG. 1, the feedthru 55 is assembled into the can wall 65 and electrically coupled to the electronic components 17 in the can 15 and the lead connector blocks 20 in the header 10. The can wall 65, which is electrically coupled to the feedthru housing 115, is in electrical communication with the ground side 91 of the chip capacitor 90 via the ground circuit extending through the feedthru housing and ground trace 145. Similarly, to the electronic components 17 in the can 15 and the lead connector blocks 20 in the header 10 are in electrical communication with each other and the power side 92 of the chip capacitor 90 via the power circuit formed by the tabs 70, their respective vias 142 and the power trace 150.

Figure 8A:
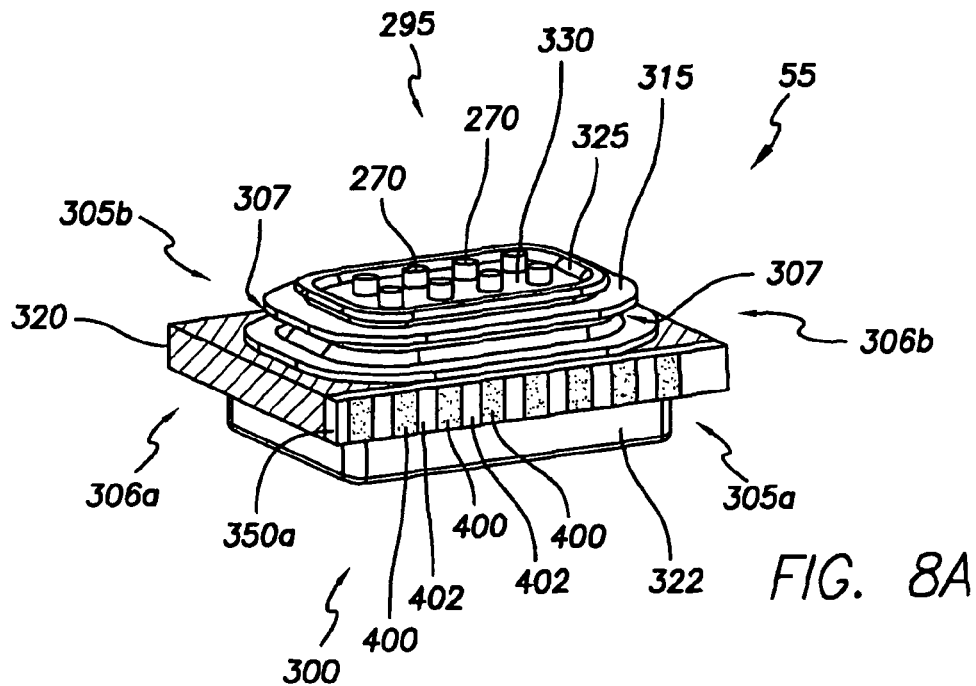
FIG. 8A is a side-top isometric view of the feedthru.
Figure 8B:
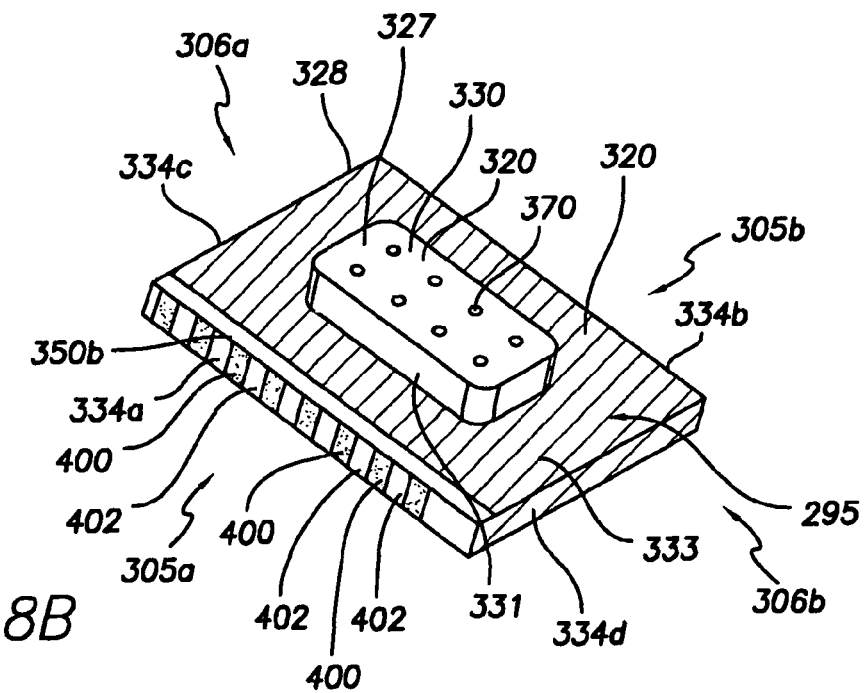
FIG. 8B is another side-top isometric view of the feedthru with the housing hidden to reveal the core.
Figure 8C:
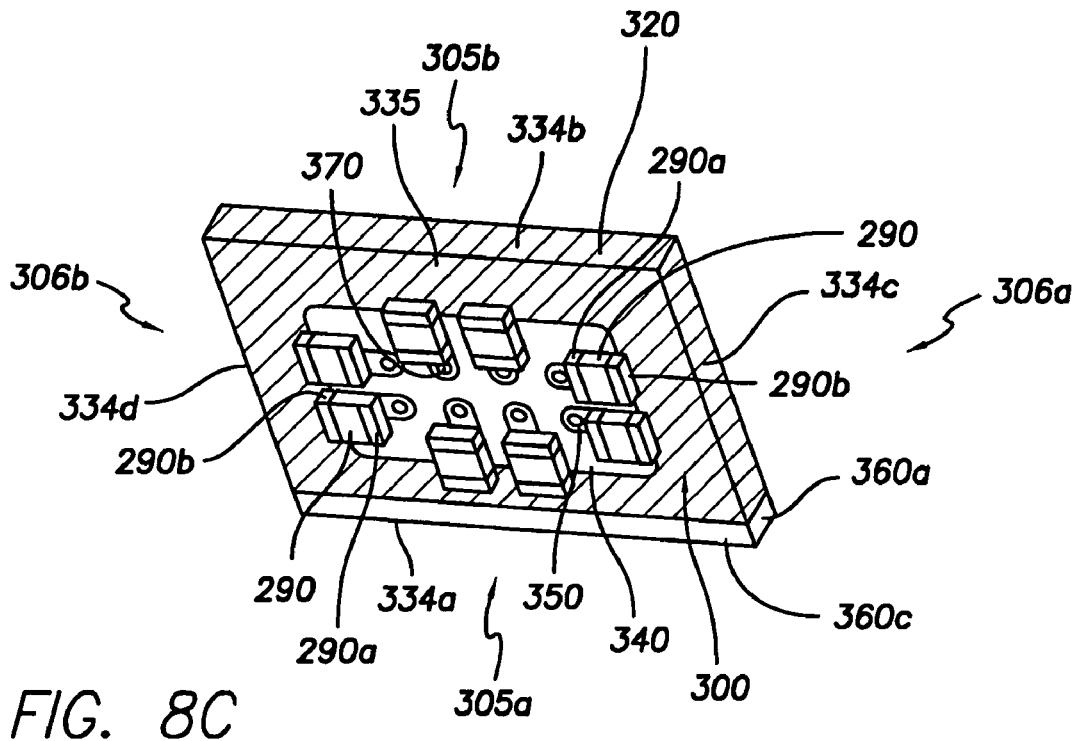
FIG. 8C is a side-top isometric view of the feedthru with the shield hidden to reveal the chip capacitors.
Figure 8D:
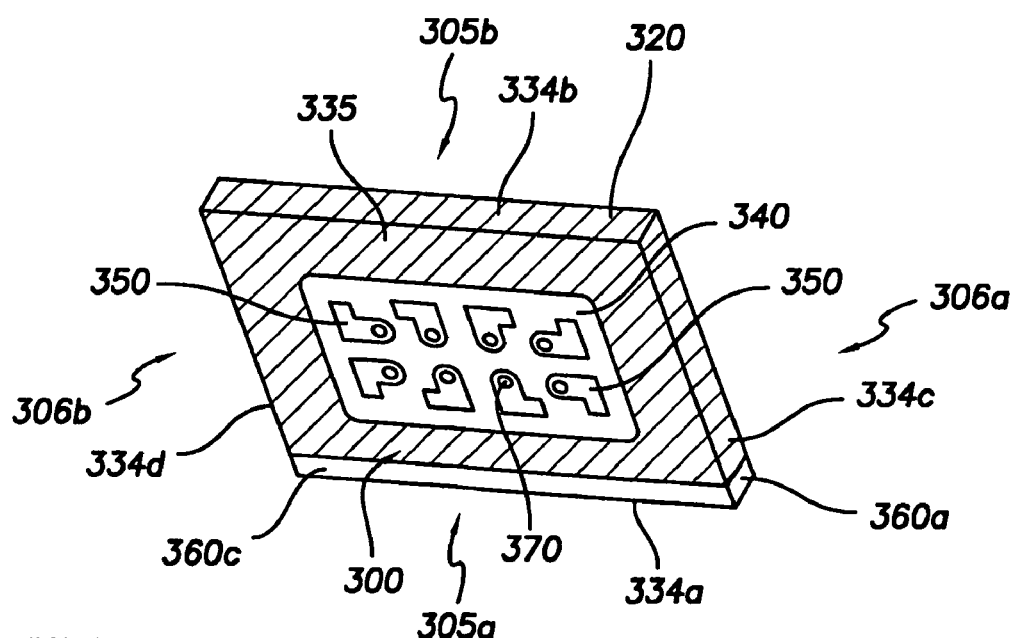
FIG. 8D is the same view as FIG. 8C, except the chip capacitors are hidden to reveal the power traces.
Figure 9A:
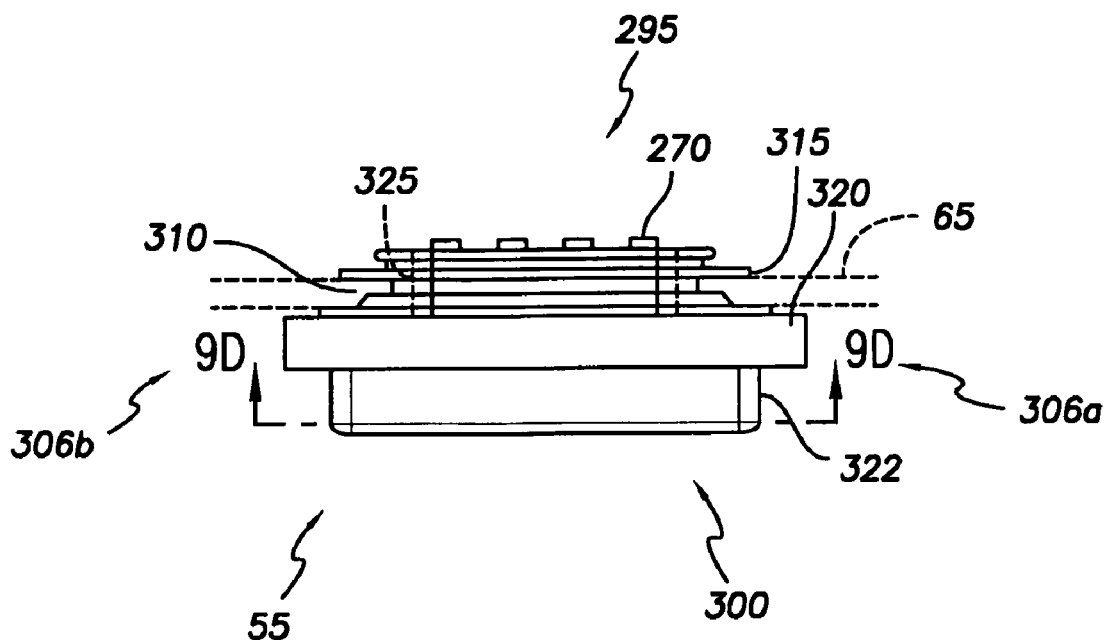
FIG. 9A is an elevation view of the non-contact side of the feedthru.
Figure 9B:
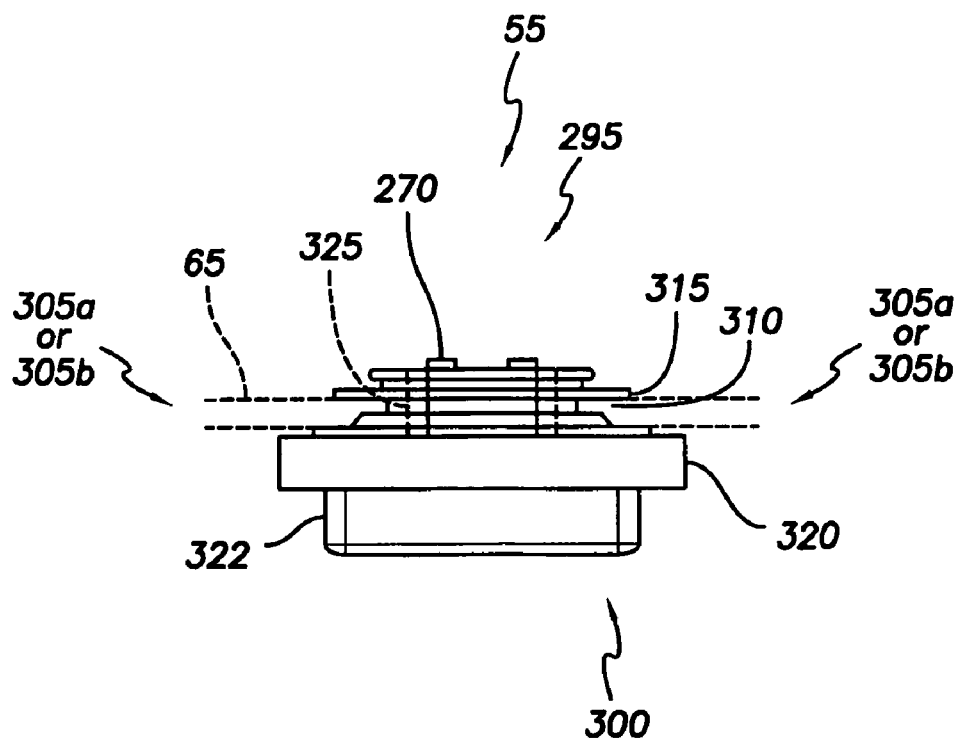
FIG. 9B is an elevation view of one of the ends of the feedthru.
Figure 9C:
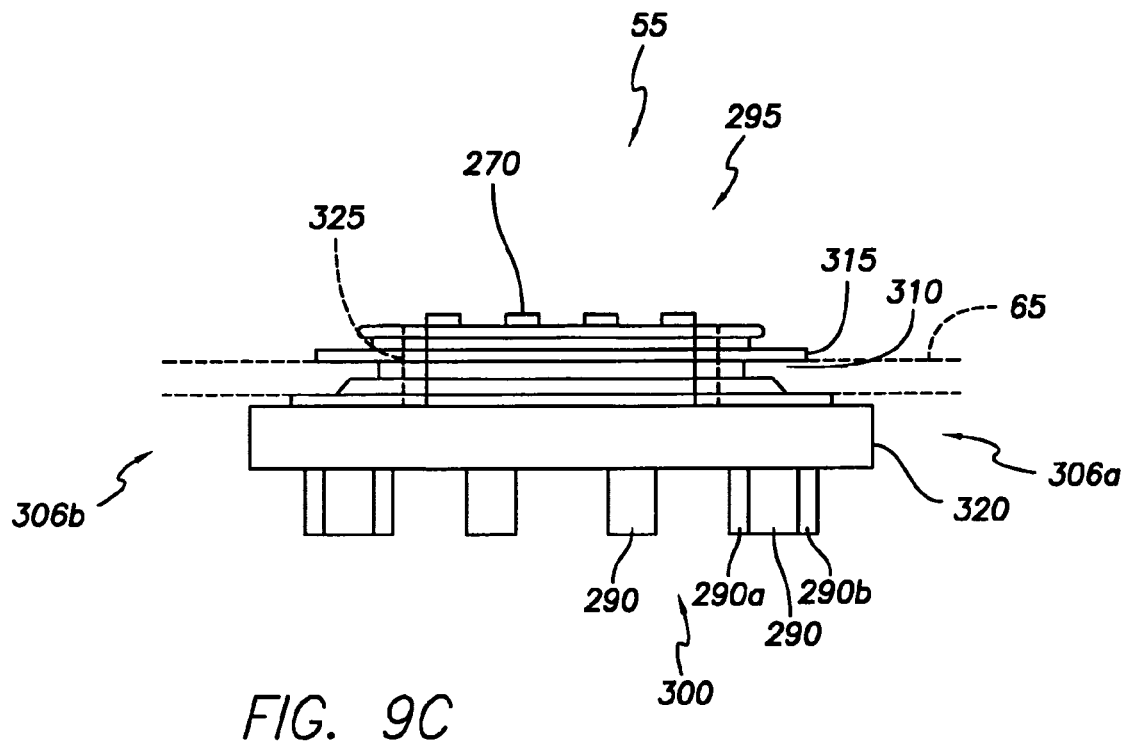
FIG. 9C is the same elevation view of FIG. 9A, less the shield.
Figure 9D:
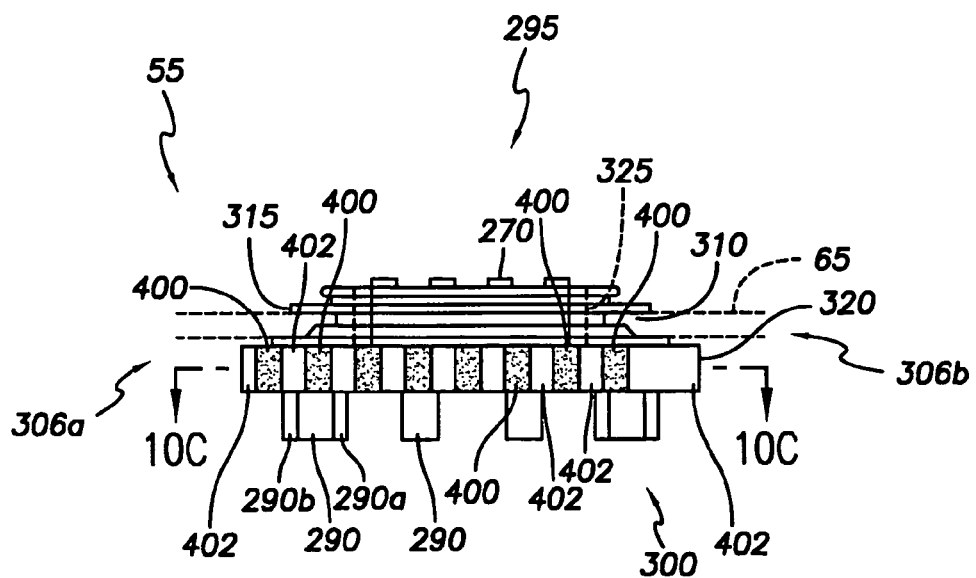
FIG. 9D is an elevation view of the contact side of the feedthru, less the shield.

To begin a detailed discussion regarding another embodiment of a feedthru 55 that may be employed with a pulse generator 5 similar to that depicted in FIG. 1, reference is now made to FIGS. 8A-8D and 9A-9D. FIG. 8A is a side-top isometric view of the feedthru 55, and FIG. 8B is another side-top isometric view of the feedthru 55 with the housing 315 hidden to reveal the core 320. FIG. 8C is a side-top isometric view of the feedthru 55 with the shield 322 hidden to reveal the chip capacitors 290, and FIG. 8D is the same view as FIG. 8C, except the chip capacitors 290 are hidden to reveal the power traces 350. FIGS. 9A and 9B are, respectively, an elevation view of the non-contact side 305b of the feedthru 55 and an elevation view of one of the ends (306a or 306b) of the feedthru 55. FIGS. 9C and 9D are, respectively, the elevation view of FIG. 9A less the shield 322 and an elevation view of the contact side 305a of the feedthru 55 less the shield 322.

In one embodiment, as shown in FIGS. 8A-9D, the feedthru 55 includes a header side 295, a can side 300, a contact side 305a, a non-contact side 305b, and first and second ends 306a, 306b. As can be understood from FIGS. 8A-8C, the overall configuration of the feedthru 55 may be generally rectangular in some embodiments. However, in other embodiments, similar to as discussed above with respect to the preceding embodiments, the feedthru 55 may have other configurations.

As illustrated in FIGS. 8A-9D, in one embodiment, the feedthru 55 includes a feedthru housing 315, a core 320, a shield 322, chip capacitors 290, tabs 270 and ground and power circuits. The housing 315 has an outer contoured side 307 and a central or core-receiving opening 325. The contoured side 307 of the housing 315 includes the groove or slot 310 that receives the can wall 65 when the feedthru is mounted in the can wall. The central opening 325 of the housing 315 extends axially through the housing and defines a void that is occupied by the core 320, or more specifically, as described below, an upper portion 327 of the core 320. The housing 315 may be machined, molded or otherwise formed to fit the space and design constraints of an implantable pulse generator 5. The housing 315 may be titanium, a titanium alloy, MP35N, or stainless steel.

As can be understood from FIG. 8B, in one embodiment, the core 320 includes an upper necked-down portion 327 extending from a bottom base portion 328. As indicated in FIGS. 8B-8D, the upper portion 327 includes a header face 330 and sides 331, and the base portion 328 includes an upper surface 333, side surfaces 334a, 334b, end surfaces 334c, 334d, and a can face 335. The sides 331 of the upper portion 327 extend generally perpendicularly between the header face 330 and the upper surface 333 of the base portion 328. The sides 331 of the upper portion 327 are configured such that the upper portion 327 may be matingly received in the core-receiving opening 325 of the housing 315. When the upper core portion 327 is fully received in the core-receiving opening 325, a bottom surface or boundary of the housing 315 may abut against the upper surface 333 of the core base portion 328, as indicated in FIGS. 8A and 9A-9D. The core 320 may also include vias or through-holes 370 extending axially therethrough. The core 320 may be formed of an electrically insulating material, such as ceramic, glass, sapphire, ceramic 99% minimum pure alumina, or etc.

As can be understood from FIGS. 8A-8D, an electrically conductive material (represented by the cross-hatching in FIGS. 8A-8D) may extend across and form at least a portion of one or more of the following surfaces of the base portion 328 of the core 320: the upper surface 333; the side surface 334b corresponding to the non-contact side 305b of the feedthru 55; the end surfaces 334c, 334d; and the can face 335. Where the surfaces 333, 334b, 334c and 335 or at least portions thereof are formed by the conductive material (represented by cross-hatching), the surfaces 333, 334b, 334c and 335 or at least portions thereof may be electrically conductive and form at least a portion of a ground circuit as discussed later in this Detailed Description. The electrically conductive material (represented by cross-hatching) may be formed of gold, nickel, platinum, electrolytic nickel and gold, etc., where such coating is provided via electroplating, photo deposition, vapor deposition, etc. In one embodiment, the conductive material shall be in the form of a plating having a minimum thickness of 75 micro inches.

As indicated in FIG. 8B, in one embodiment, the conductive material (represented by cross-hatching) may extend across the entirety of an end surface 334d. However, as indicated in FIGS. 8A, 8C and 8D, the conductive material (represented by cross-hatching) may extend across less than the entirety of an end surface 334c, ending a short distance from the side surface 334a corresponding to the contact side 305a of the feedthru 55 such that this region 360a of the side surface 334c may be the electrically insulating surface of the electrically insulating material forming the core 320, defining an electrical insulation surface 360a.

As indicated in FIG. 8B, in one embodiment, the conductive material (represented by cross-hatching) may extend across less than the entirety of the upper surface 333, ending a short distance from the side surface 334a corresponding to the contact side 305a of the feedthru 55 such that this region 360b of the upper surface 333 may be the electrically insulating surface of the electrically insulating material forming the core 320, defining an electrical insulation surface 360b. The upper portion 327 of the core 320 may be completely free of the conductive material (represented by cross-hatching).

As indicated in FIG. 8D, in one embodiment, the conductive material (represented by cross-hatching) may extend across the entirety of regions of the can face 335 near three of the four edges of the can face 335, a rectangular central region 340 of the can face 335 being free of the conductive material (represented by cross-hatching) such that the surface of the central region 340 may be the electrically insulating surface of the material forming the core 320. Near the fourth edge of the can face 335, the conductive material (represented by cross-hatching) extending across the can face 335 may end a short distance from the side surface 334a corresponding to the contact side 305a of the feedthru 55 such that this region 360c of the can face 335 may be the electrically insulating surface of the electrically insulating material forming the core 320, defining an electrical insulation surface 360c.

As shown in FIG. 8D, the central region 340 of the can face 335 may include one or more traces 350, which may be L-shaped or other shapes. Each trace 350 may be spaced apart from adjacent traces 350 and the electrically conductive material (represented by cross-hatching) surrounding the central region 340. The traces 350 may be formed of an electrically conductive material such as gold, nickel, platinum, etc., where such coating is provided via electroplating, photo deposition, vapor deposition, etc. Because the traces 350 are separated from each other and the electrically conductive material (represented by cross-hatching) surrounding the central region 340, each trace 350 is electrically isolated until a chip capacitor 290 is placed to extend between the trace 350 and the electrically conductive material (represented by cross-hatching) surrounding the central region 340, as illustrated in FIG. 8C. For example, a power side 290a of a chip 290 may be electrically connected to a respective trace 350, and a ground side 290b of the chip capacitor 290 may be electrically connected to a location on the electrically conductive material (represented by cross-hatching) surrounding the central region 340. Since the electrically conductive material (represented by cross-hatching) surrounding the central region 340 extends about the side surfaces 334b-334d to the upper surface 333, which is in electrical contact with the housing 315 that is in electrical contact with the can wall 65 (see FIGS. 9A-9D), the combination of the chip capacitor ground side 290b, the conductive surfaces 334b-334d and 333 of the core 320, the housing 315, and the can wall 65 may form the ground circuit of the feedthru 55 and the pulse generator 5.

As can be understood from FIGS. 8A, 9A and 9B, the shield 322 may extend downward from, and be in electrical contact with, the electrically conductive material (represented by cross-hatching in FIGS. 8C and 8D) of the can face 335. The shield 322 may further extend below the capacitor chips 290 to totally enclose the capacitor chips 290 in a volume defined by the interior of the shield 322 and the can face 335. The shield 322 may be formed of titanium, stainless steel, nickel, etc., have a thickness of between approximately 0.005' and approximately 0.01", and be used to shield undesired EMI signals from entering the can 15.

The through-holes or vias 370 may terminate on the upper or header side of the feedthru 55 at the header face 330 of the core 320, as depicted in FIG. 8B. Similarly, each through-hole or via 370 may terminate on the bottom or can side of the feedthru 55 at the can face 335 of the core 320, as depicted in FIG. 8D. More specifically, as shown in FIG. 8D, a through-hole or via 370 may terminate in a portion of each trace 350.

Figure 10A:
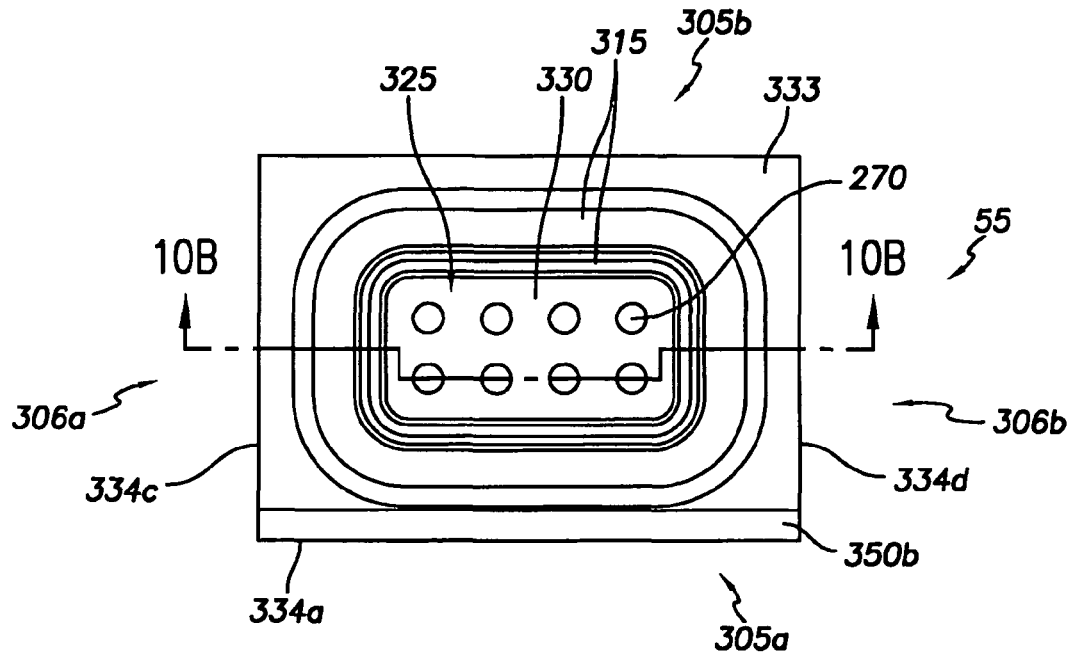
FIG. 10A is a plan view of the header side of the feedthru.
Figure 10B:
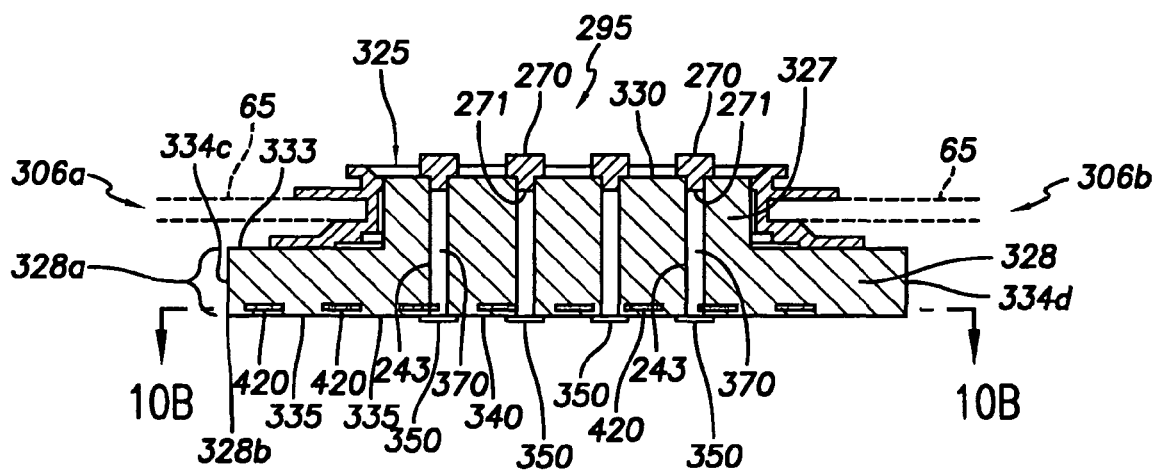
FIG. 10B is a longitudinal cross-section elevation of the feedthru as taken along section line 10B-10B in FIG. 10A.

As can be understood from FIG. 8A and FIG. 10A, which is a plan view of the header side of the feedthru 55, there may be one or more electrically conductive tabs 270 and, in one embodiment, there may be eight tabs 270 arranged in two spaced apart rows of four tabs 270. As indicated in FIGS. 8B and 8D, the electrically conductive vias 370 may be in a similar arrangement of two rows of four vias 370. Thus, a tab 270 may extend from the header side of each respective via 370. More specifically, as depicted in FIG. 10B, which is a longitudinal cross-section elevation of the feedthru 55 as taken along section line 10B-10B in FIG. 10A, a portion of each tab 270 may extend downward into the upper end of each respective via 370. In other embodiments, the tabs 270 and vias 370 may be located in other configurations or locations as long as there is sufficient space for connection of the conductors 60 (see FIG. 1) to the tabs 270 on the header side of the feedthru 55.

As indicated in FIG. 10B, in one embodiment, the electrically conductive tabs 270 and electrically conductive vias 370 may be configured in a manner similar to that discussed above with respect to FIG. 6E. Specifically, the tabs 270 may partially extend as nubs 271 into the vias 370. The vias 370 may be in the form of electrically conductive through-holes 370 lined with electrically conductive coatings 243 that serve as vias 370 that complete the electrical connections between the nubs 271 and the traces 350 in the central region 340 of the can side 300 of the feedthru 55. The surfaces of the through-holes 370 may be coated with an electrically conductive material 243, such as gold, nickel, platinum, etc., where such coating is provided via electroplating, photo deposition, vapor deposition, etc. The tabs 270 may be made of titanium, kovar, stainless steel, MP35N, platinum or gold. The nubs 271 may be brazed (including gold brazed), welded or epoxied into the through-holes 370.

In other embodiments, the vias 370 may be solid members distinct from, but electrically contacting, the tabs 270 and extending through the core 320 similar to those discussed above with respect to FIG. 6A. In such embodiments the solid member vias 370 may be formed of electrically conductive material such as titanium, stainless steel, MP35N, etc. or a solid member formed of electrically or non-electrically conductive material coated with an electrically conductive material, such as gold, nickel, platinum, etc., where such coating is provided via electroplating, photo deposition, vapor deposition, etc. Such solid member vias 370 may be brazed (including gold brazed), welded or epoxied into the holes in the core 320, and the tabs 270 may be similarly attached to the solid member vias.

In yet other embodiments, the vias 370 may be solid members that are extensions of the tabs 270 and extending through the core 320 similar to those discussed above with respect to FIGS. 6B and 6F. In yet other embodiments, the arrangement may be similar to that discussed above with respect to FIG. 6D, wherein the vias 370 may be through-holes 370 lined with an electrically conductive coating 243 (see FIG. 10B), but wherein the tabs 270 do not have nubs 271 or extensions that extend into the vias 370.

While the electrically conductive tabs 270 illustrated in FIG. 8A have a generally cylindrical shape similar to that described above with respect to FIGS. 7G and 7H, in other embodiments the tabs 270 may have other shapes. For example, the tabs 270 may have a hemispherical, reduced profile shape as discussed above with respect to FIGS. 7C and 7D, a less reduced profile hemispherical shape as discussed with respect to FIGS. 7E and 7F, a nub or planar configuration as discussed above with respect to FIGS. 7A and 7B, or a cubical or rectangular post like shape as discussed above with respect to FIGS. 2A and 5A. In other embodiments, the post-like tabs 270 may have other shapes or configurations, such as cubical, half-spherical, cylindrical or some other shape. The tabs 270 may have other configurations, and regardless of their shape, simply serve as locations or features for welding, brazing or other types of attachment to the conductors 60 of the header 10. While the via configuration and tab configuration depicted in FIGS. 8A and 10B are consistent among the pairs of vias and tabs, in other embodiments, the via and tab configurations employed for a single feedthru 55 may be of a variety of types and may be mixed and matched.

As shown in FIGS. 8A, 8B and 9D, the side surface 334a of the base portion 328 corresponding to the contact side 305a may include one or more electrical contact surfaces 400. For example, there may be a plurality of electrical contact surfaces 400 generally evenly distributed in a spaced-apart fashion along the length of the side surface 334a, the electrical contact surfaces 400 being electrically isolated from each other via insulation surfaces 402 located between each pair of electrical contact surfaces 400. As a result, the side surface 334a may have a striped arrangement of electrical contact surfaces 400 and electrical insulation surfaces 402. In one embodiment, the electrical contact surfaces 400 may be generally planar surfaces of the side surface 334a of the core base portion 328 that are coated or plated with an electrically conductive material such as gold, nickel, platinum, electrolytic nickel and gold, etc., where such coating is provided via electroplating, photo deposition, vapor deposition, etc. In one embodiment, the conductive material forming the surfaces 400 shall be in the form of a plating having a minimum thickness of 75 micro inches.

The electrical insulation surfaces 402 may be generally planar surfaces of the side surface 334a of the core base portion 328 that are free from any electrically conductive coating. Because of the electrical insulation surfaces 402, 360a, 360b, and 360c, the electrical contact surfaces 400 are electrically isolated from each other and the adjacent electrically conductive portions of the surfaces 295, 300, 360a, and 360b of the core lower portion 328.

Figure 10C:
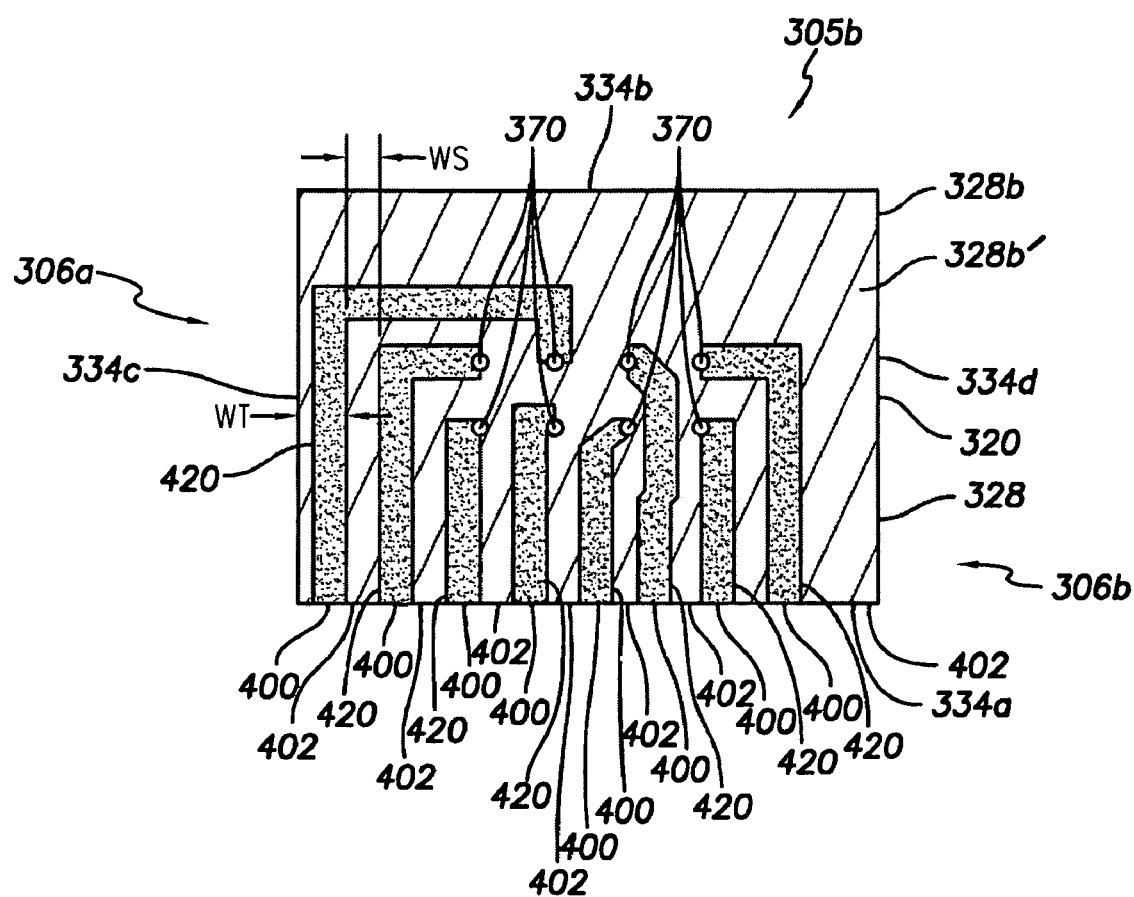
FIG. 10C is a cross-section plan view of the feeder traces extending through the core as taken along section line 10C-10C in FIGS. 9D and 10B.

As indicated in FIG. 10C, which is a cross-section plan view of feeder traces 420 extending through the core 320 as taken along section line 10C-10C in FIGS. 9D and 10B, feeder traces 420 may electrically connect the electrical contact surfaces 400 with the vias 370. Thus, the electrical contact surfaces 400, feeder traces 420, vias 370, power traces 350, and tabs 270 may be in electrical communication with each other and the power sides 290a of the capacitor chips 290, thereby forming a power side circuit of the feedthru 55.

Figure 11:
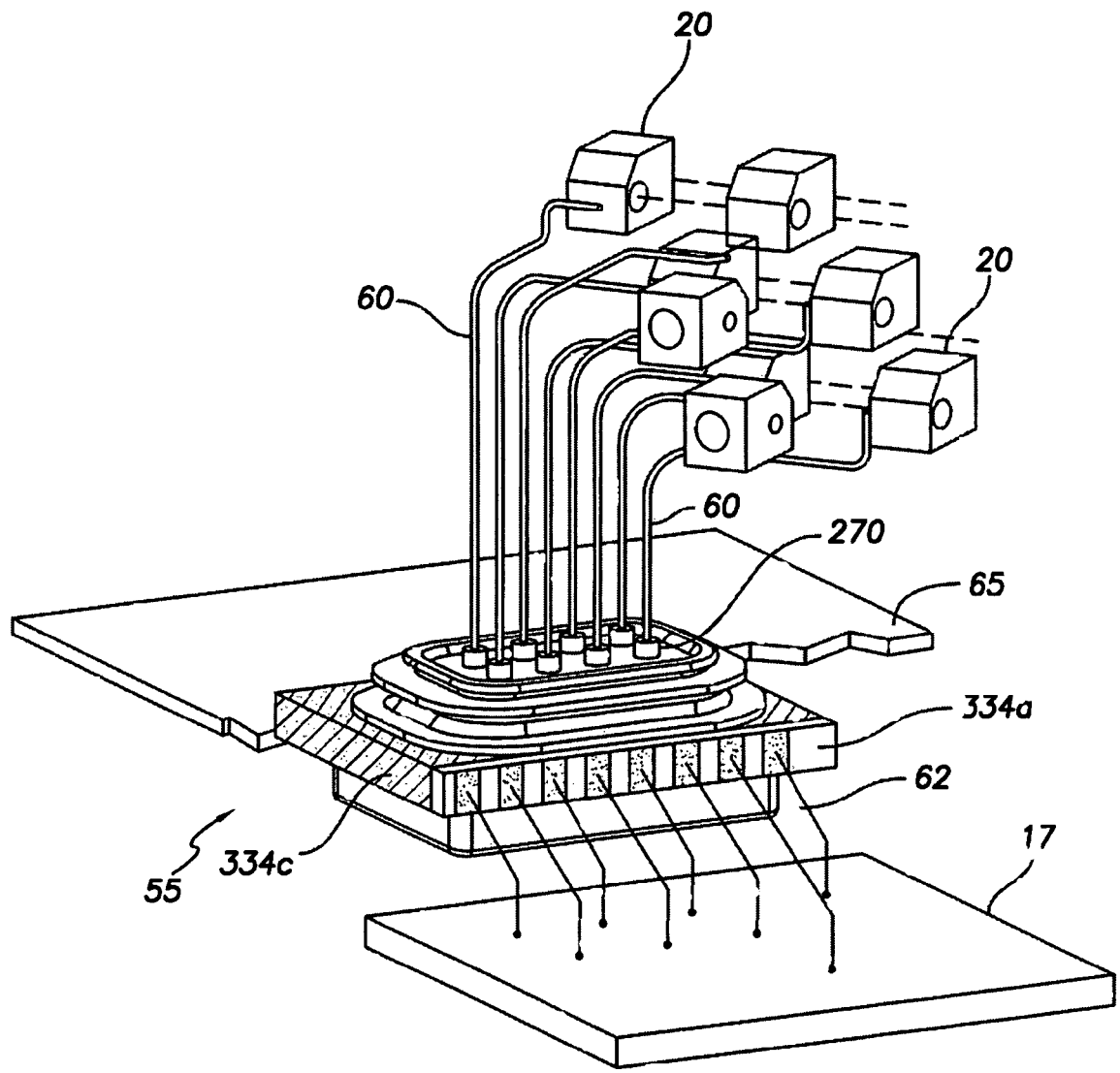
FIG. 11 is an isometric view of the feedthru of FIG. 8A mounted in the can wall of an implantable pulse generator.

As indicated in FIG. 11, which is an isometric view of the feedthru 55 of FIG. 8A mounted in the can wall 65 of an implantable pulse generator, when the feedthru 55 is installed in the pulse generator, the pulse generator's electronic components 17 (e.g., output flex, hybrid, or various other electronic components) housed within the can 15 may be electrically connected to the electrical contact surfaces 400 via conductors 62 (e.g., round wires, flat ribbon wires, flex cables, wire bond, or etc.) extending between the electrical contact surfaces 400 and the electronic components 17. Similarly, conductors 60 (e.g., round wires, flat ribbon wires, flex cables or etc.) may extend from the tabs 270 to the respective connector blocks 20 within the header of the pulse generator. Thus, the power circuit (e.g., the electrical contact surfaces 400, feeder traces 420, vias 370, power traces 350, and tabs 270) and conductors 60, 62 place the electronic components 17 in electrical communication with the connector blocks 20 and the power sides 290a of the chip capacitors 290. The ground circuit (e.g., the conductive surfaces 334b-334d and 333 of the core 320, and the feedthru housing 315) place the ground sides 290b of the chip capacitors 290 in electrical communication with the wall 65 of the can 15 of the pulse generator 5.

As shown in FIGS. 10B and 10C, one or more feeder traces 420 may extend through the core lower portion 328. The feeder traces 420 are spaced apart from each other and physically and electrically isolated from each other by the material of the core lower portion 328 that exists between the adjacent feeder traces 420.

As can be understood from FIG. 10B, in one embodiment, the core lower portion 328 may have a top section 328a (i.e., the section 328a of the core lower portion 328 located above section line 10C-10C in FIG. 10B) and a bottom section 328b (i.e., the section 328b of the core lower portion 328 located below section line 10C-10C in FIG. 10B) that are joined together via brazing, epoxy, etc. in a sandwich fashion to form a joined unitary piece core lower portion 328.

As can be understood from FIGS. 10B and 10C, in one embodiment, the feeder traces 420 may extend across an upper surface 328b' of the bottom section 328b of the core lower portion 328. Specifically, the feeder traces 420 may be formed of an electrically conductive material such as gold, nickel, platinum, electrolytic nickel and gold, etc., where such coating is provided on the upper surface 328' of the bottom section 328b of the core lower portion 328 via electroplating, photo deposition, vapor deposition, etc. In one embodiment, the conductive material shall be in the form of a plating having a minimum thickness of 75 micro inches. When being deposited on the upper surface 328b', the feeder traces 420 may be caused to be routed between locations corresponding to respective vias 370 and respective side contacts 400.

Once the feeder traces 420 are deposited on the upper surface 328b' of the bottom section 328b of the core lower portion 328 as shown in FIG. 10C, the bottom section 328b is joined to the top section 328a in the above-described sandwich fashion by abutting the upper surface 328b' of the bottom section 328b to the lower surface of the top section 328a, the feeder traces 420 being sandwiched between the top section 328a and bottom section 328b as shown in FIG. 10B.

In other embodiments, the feeder traces 420 are deposited on the lower surface of the top section 328a of the core lower portion 328, and then the lower surface of the top section 328a and the upper surface 328b' of the top section 328b are abutted together to sandwich together the top section 328a and bottom section 328b. In yet other embodiments, the feeder traces 420 are deposited on an electrically insulating substrate, which is then sandwiched between the top section 328a and the bottom section 328b.

While the feeder traces 420 are discussed above as being in the form of traces deposited on the surface of a section of the core lower portion 328 via electroplating, photo deposition, vapor deposition, etc., in other embodiments, the feeder traces 420 may be in the form of other electrical conductor configurations. For example, in some embodiments, the feeder traces 420 may be in the form of electrically conductive wires, cable, etc. that are imbedded in the core lower portion 328 during the process of molding the core lower portion 328.

In one embodiment, as can be understood from FIG. 10B, the feeder traces 420 may be imbedded in the core lower portion 328 in a plane that is approximately 0.006 inch above the can face 335 and on a level approximately equal to that depicted by section line 10C-10C in FIG. 10B.

As can be understood from FIG. 10C, in one embodiment, an individual feeder trace 420 may have a width WT of approximately 0.03 inch and be space apart from adjacent feeder traces 420 by a width WS of approximately 0.03 inch.

As can be understood from FIGS. 1 and 8A-11, in one embodiment, an implantable pulse generator 5 may include a header 25, a can 15, and a feedthru 55. The header may include a lead connector block 20 electrically coupled to a first conductor 60. The can 15 may be coupled to the header 25 and include a wall 65 and an electronic component 17 electrically connected to a second conductor 62 and housed within the wall 65. The feedthru 55 may be mounted in the wall 65 and include a header side 295, a can side 300, an electrical insulating core 320, a ground circuit, and a power circuit. The core 320 may include a first surface 330 forming at least part of the header side 295, a second surface 335 forming at least part of the can side 300, and a third surface 334a lateral to at least one of the first surface 330 and second surface 335.

As can be understood from FIGS. 10B, 10C and 11, the power circuit may extend through the core 320 from the third surface 334a to the first surface 330. The first conductor 60 may be electrically connected to the power circuit near the first surface 330, and the second conductor 62 may be electrically connected to the power circuit near the third surface 334a. As can be understood from FIGS. 8C, 8D and 11, at least a portion of the ground circuit may extend along the second surface 335 and is electrically coupled to the wall 65.

As indicated in FIGS. 10B and 10C, the power circuit may include a first portion 370 extending through the core 320 between the first surface 330 and the second surface 335. The power circuit may further include a second portion 420 extending generally laterally through the core 320 from the third surface 334a to the first portion 330.

As indicated in FIG. 8C, the feedthru 55 may also include a chip capacitor 290. The second surface 335 may include an electrically conductive layer 350 electrically connected to a portion 370 of the power circuit and spaced apart from the at least a portion (represented by cross-hatching) of the ground circuit extending along the second surface 335. The chip capacitor 290 may electrically span between the electrically conductive layer 350 and the at least a portion (represented by cross-hatching) of the ground circuit extending along the second surface 335.

Although the present invention has been described with reference to preferred embodiments, persons skilled in the art will recognize that changes may be made in form and detail without departing from the spirit and scope of the invention.

What is claimed is:

1. An implantable pulse generator comprising: a header including a lead connector block electrically coupled to a first conductor; a can coupled to the header and including a wall and an electronic component electrically connected to a second conductor and housed within the wall; and a feedthru mounted in the wall and including a header side, a can side, an electrical insulating core, a ground circuit, and a power circuit; wherein the core includes a first surface forming at least part of the header side, a second surface forming at least part of the can side, and a third surface lateral to at least one of the first and second surfaces, and wherein the third surface is disposed within the can; wherein the power circuit extends through the core from the third surface to the first surface and the first conductor is electrically connected to the power circuit near the first surface and the second conductor is electrically connected to the power circuit near the third surface; wherein at least a portion of the ground circuit extends along the second surface and is electrically coupled to the wall; and wherein the third surface comprises at least one electrical contact surface, and wherein the electrical component is directly connected to the at least one electrical contact surface by the second conductor.

2. The pulse generator of claim 1, wherein the power circuit includes a first portion extending through the core between the first surface and the second surface.

3. The pulse generator of claim 2, wherein the first portion includes a via including at least one of a through hole including an electrically conductive layer and a solid electrically conductive member.

4. The pulse generator of claim 2, wherein the power circuit further includes a second portion extending generally laterally through the core from the third surface to the first portion.

5. The pulse generator of claim 4, wherein the second portion includes at least one of a trace and a solid wire.

6. The pulse generator of claim 1, wherein the third surface includes an electrically conductive layer electrically connected to the power circuit and to which the second conductor is electrically connected.

7. The pulse generator of claim 1, further comprising a chip capacitor and wherein the second surface includes an electrically conductive layer electrically connected to the power circuit and spaced apart from the at least a portion of the ground circuit extending along the second surface, the chip capacitor electrically spanning between the electrically conductive layer and the at least a portion of the ground circuit extending along the second surface.

8. The pulse generator of claim 1, wherein the first surface includes an electrically conductive tab electrically connected to the power circuit and to which the first conductor is electrically connected.

9. The pulse generator of claim 8, wherein the tab is post-like.

10. The pulse generator of claim 9, wherein the post-like tab is at least one of generally cubical, generally cylindrical and generally half-spherical.

11. The pulse generator of claim 8, wherein the tab is of a low relief relative to the first surface.

12. The pulse generator of claim 11, where the tab is of such low relief as to be at least nearly flush with the first surface.

13. The pulse generator of claim 1, wherein the core is formed of a ceramic material.

14. The pulse generator of claim 1, wherein at least one of the first conductor and second conductor is at least one of round wire, flat ribbon wire, flex cable, and wire bond.

15. The pulse generator of claim 1, wherein the second conductor is at least one of a round wire, flat ribbon wire, and flex cable.

16. The pulse generator of claim 1, wherein the at least one electrical contact surface comprises a plurality of electrical contact surfaces, wherein the second conductor comprises a plurality of conductors, wherein the electrical component comprises a plurality of electrical components, and wherein each of the plurality of electrical components are directly connected to one of the respective plurality of electrical contact surfaces by one of the plurality of respective conductors.

17. An implantable pulse generator comprising: a header including a lead connector block electrically coupled to a first conductor; a can coupled to the header and including a wall and an electronic component electrically connected to a second conductor and housed within the wall; a feedthru mounted in the wall including a header side, a can side, and comprising an electrically insulating core and a power circuit; and a chip capacitor mounted on the feedthru; wherein the core includes a first side forming at least part of the header side, a second side forming at least part of the can side, and a third side generally lateral the second side, and wherein the third side is disposed within the can; wherein the power circuit extends between the three sides, the first conductor being electrically connected to the power circuit at the first side, the second conductor being electrically connected to the power circuit at the third side, and a power side of the chip capacitor being electrically connected to the power circuit at the second side; and wherein the third side comprises at least one electrical contact surface, and wherein the electrical component is directly connected to the at least one electrical contact surface by the second conductor.

18. The pulse generator of claim 17, further comprising a ground circuit extending from a ground side of the chip capacitor to the wall, at least a part of the ground circuit extending along a surface of the core.

19. The pulse generator of claim 18, wherein the surface of the core includes at least a portion of the second side.

20. The pulse generator of claim 17, wherein the power circuit extending between the three sides includes at least a portion of the power circuit extending through the core.

21. The pulse generator of claim 20, wherein the at least a portion of the power circuit includes a via extending between the first side and the second side.

22. The pulse generator of claim 21, wherein the at least a portion of the power circuit includes a trace extending between the via and the third side.

23. The pulse generator of claim 17, wherein the second conductor is at least one of a round wire, flat ribbon wire, and flex cable.

24. The pulse generator of claim 17, wherein the at least one electrical contact surface comprises a plurality of electrical contact surfaces, wherein the second conductor comprises a plurality of conductors, wherein the electrical component comprises a plurality of electrical components, and wherein each of the plurality of electrical components are directly connected to one of the respective plurality of electrical contact surfaces by one of the plurality of respective conductors.

* * * * *